(12) United States Patent
Ostfeld et al.

(10) Patent No.: US 8,932,262 B2
(45) Date of Patent: *Jan. 13, 2015

(54) INDWELLING DEVICE

(71) Applicants: Ishay Ostfeld, Ramnat Gan (IL); Eran Hirsziwicz, Ramat Chen (IL)

(72) Inventors: Ishay Ostfeld, Ramnat Gan (IL); Eran Hirsziwicz, Ramat Chen (IL)

(*) Notice: Subject to any disclaimer, the term of this patent is extended or adjusted under 35 U.S.C. 154(b) by 0 days.

This patent is subject to a terminal disclaimer.

(21) Appl. No.: 13/951,647

(22) Filed: Jul. 26, 2013

(65) Prior Publication Data
US 2013/0310769 A1  Nov. 21, 2013

Related U.S. Application Data

(63) Continuation-in-part of application No. 12/591,952, filed on Dec. 4, 2009, now Pat. No. 8,523,823, which is a continuation of application No. 10/916,631, filed on Aug. 12, 2004, now abandoned, which is a continuation-in-part of application No. 10/074,017, filed on Feb. 14, 2002, now abandoned.

(51) Int. Cl.
| | |
|---|---|
| *A61M 5/00* | (2006.01) |
| *A61M 25/00* | (2006.01) |
| *A61B 19/08* | (2006.01) |
| *A61M 25/01* | (2006.01) |
| *A61N 1/05* | (2006.01) |
| *A61F 2/86* | (2013.01) |
| *A61B 19/00* | (2006.01) |
| *A61F 2/00* | (2006.01) |

(52) U.S. Cl.
CPC ....... *A61M 25/0043* (2013.01); *A61M 25/0017* (2013.01); *A61B 19/081* (2013.01); *A61M 25/0111* (2013.01); *A61N 1/05* (2013.01); *A61F 2/86* (2013.01); *A61B 19/38* (2013.01); *A61N 1/056* (2013.01); *A61B 2019/082* (2013.01); *A61F 2002/009* (2013.01); *A61F 2250/0059* (2013.01); *A61F 2250/0069* (2013.01); *A61F 2250/0071* (2013.01); *A61F 2250/0092* (2013.01)
USPC .......................................................... 604/171

(58) Field of Classification Search
CPC .................. A61M 25/06668; A61M 39/0247; A61M 2025/1081; A61M 2039/0261; A61M 2039/0279; A61M 25/0017; A61M 25/0111; A61M 27/00; A61M 25/0668
USPC .................................. 604/171, 192, 349, 544
See application file for complete search history.

(56) References Cited

U.S. PATENT DOCUMENTS

| | | | | | |
|---|---|---|---|---|---|
| 3,421,509 | A | * | 1/1969 | Fiore | 604/171 |
| 3,683,928 | A | * | 8/1972 | Kuntz | 604/171 |

(Continued)

*Primary Examiner* — Nicholas Lucchesi
*Assistant Examiner* — Diva K Chander
(74) *Attorney, Agent, or Firm* — Browdy and Neimark, PLLC

(57) ABSTRACT

The present invention provides a medical device for insertion into a body, the device having at least one surface covered by and attached to at least one detachable cover and at least one surface hole, such as the cover encapsulate and seals the medical device. The cover can be detached and pulled off the device which remains in the body. The cover includes at least one sealing element for preventing ingress of fluids between the cover and at least part of the medical device. The cover and the at least one sealing element, encapsulates the medical device though it's length, overlapping at least one surface hole.
The cover and the at least one sealing element are designed to isolate at least one hole from at least another holes, while enabling free passage through it, in at least partial time period in which the medical device is within the body.

21 Claims, 44 Drawing Sheets

(56) References Cited

U.S. PATENT DOCUMENTS

| | | | |
|---|---|---|---|
| 3,854,483 A * | 12/1974 | Powers | 604/172 |
| 3,894,540 A * | 7/1975 | Bonner, Jr. | 604/171 |
| 4,692,154 A * | 9/1987 | Singery et al. | 604/172 |
| 5,792,114 A * | 8/1998 | Fiore | 604/171 |
| 6,090,075 A * | 7/2000 | House | 604/172 |
| 7,380,658 B2 * | 6/2008 | Murray et al. | 206/364 |
| 7,601,158 B2 * | 10/2009 | House | 606/108 |
| 7,918,831 B2 * | 4/2011 | House | 604/192 |
| 7,938,838 B2 * | 5/2011 | House | 606/108 |
| 2007/0161971 A1 * | 7/2007 | House | 604/544 |
| 2008/0097411 A1 * | 4/2008 | House | 604/544 |
| 2008/0097463 A1 * | 4/2008 | House | 606/108 |
| 2008/0125757 A1 * | 5/2008 | Gobel | 604/544 |
| 2008/0200907 A1 * | 8/2008 | Nestenborg | 604/544 |
| 2010/0030197 A1 * | 2/2010 | House | 604/544 |
| 2011/0213344 A1 * | 9/2011 | House | 604/544 |

* cited by examiner

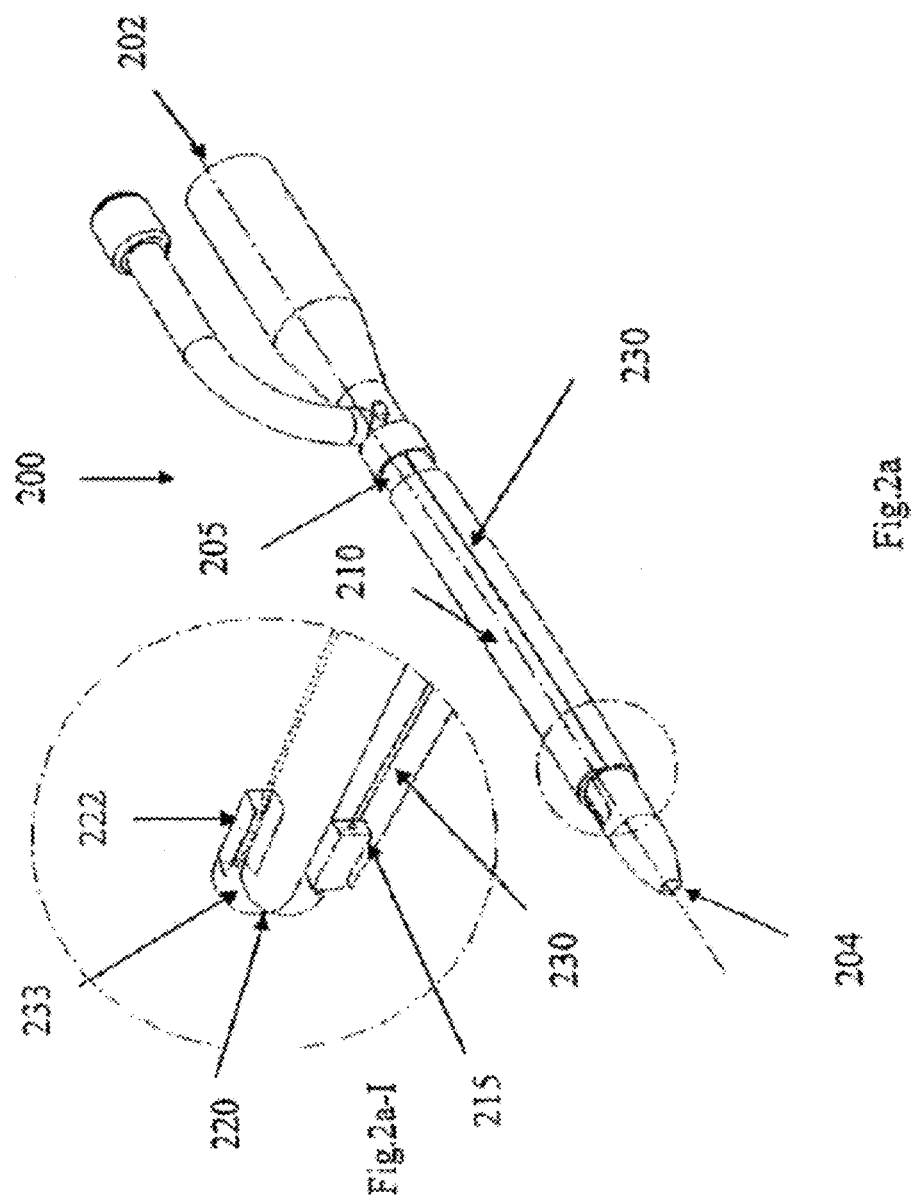

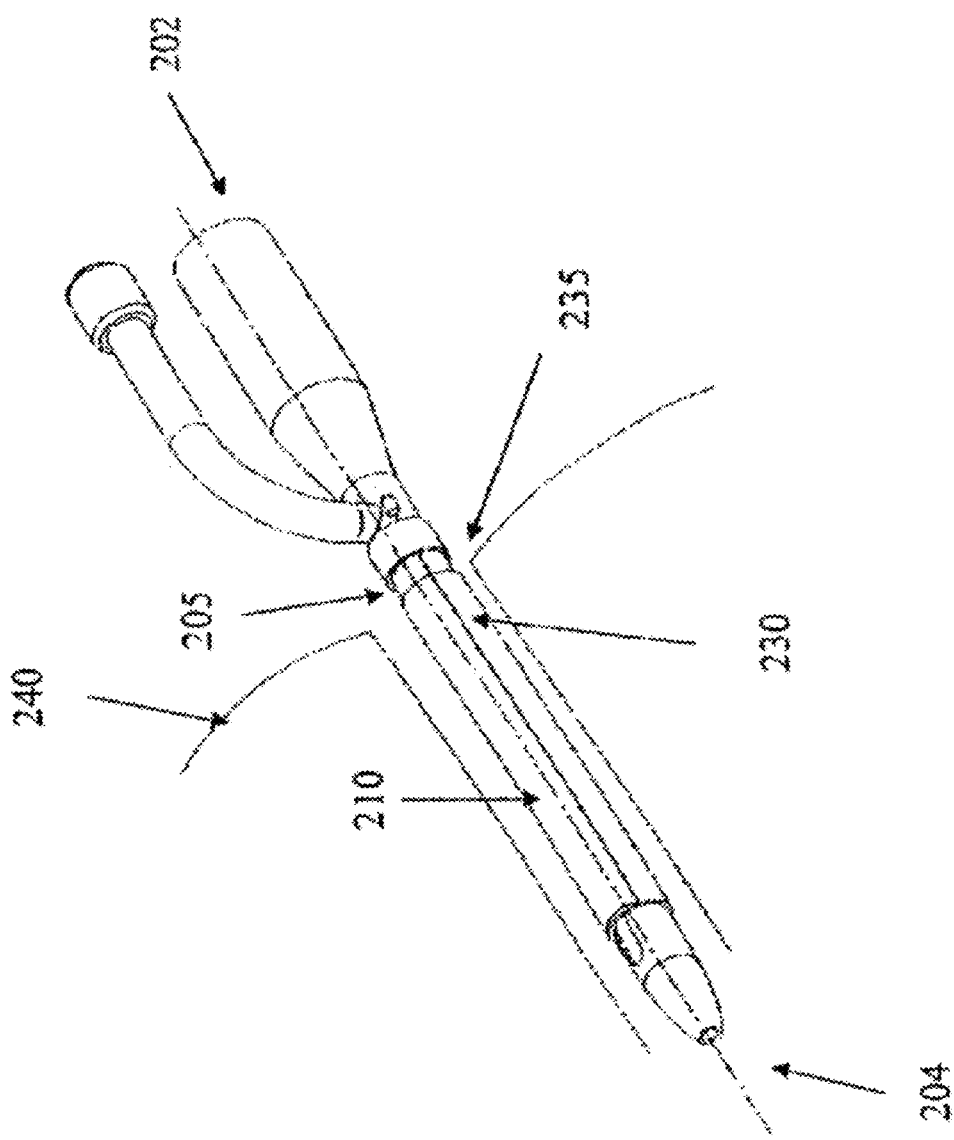

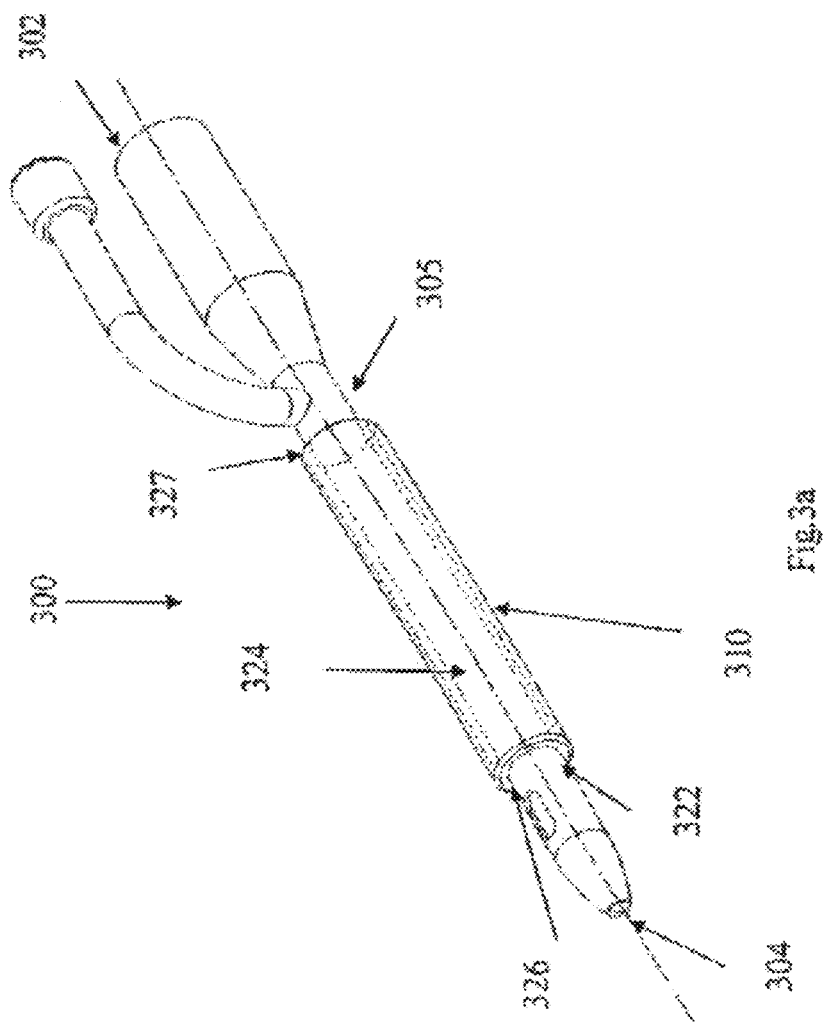

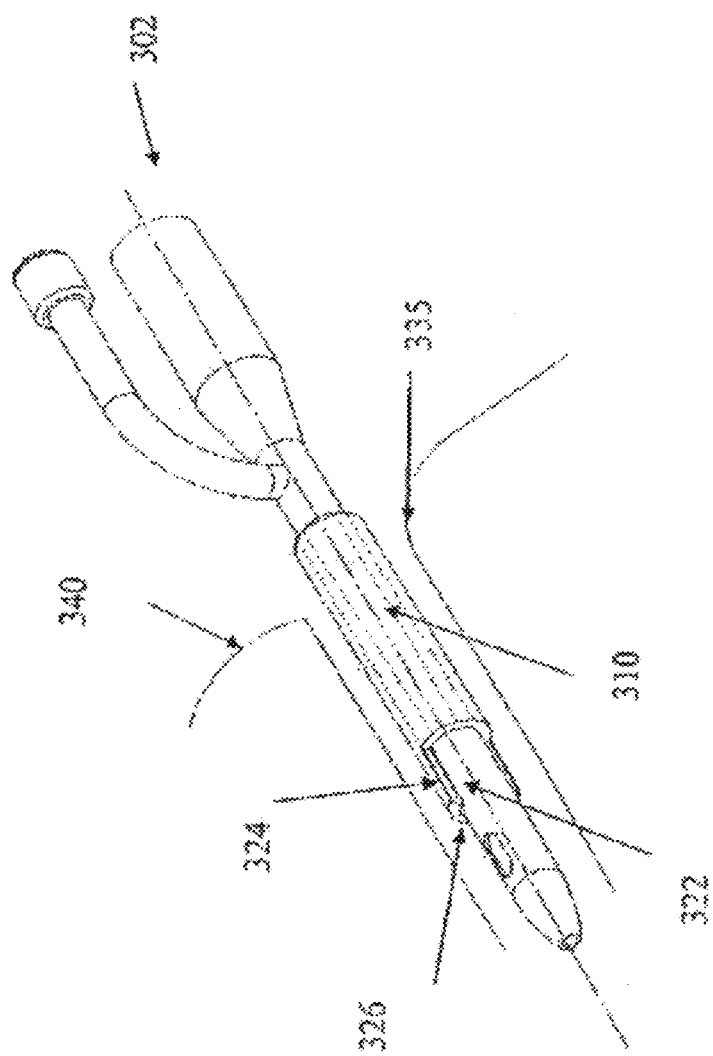

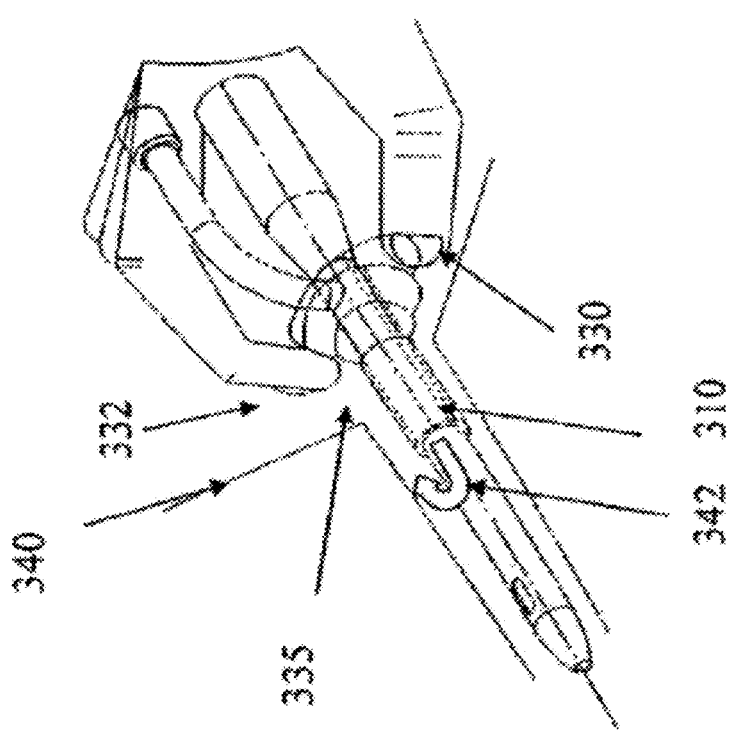

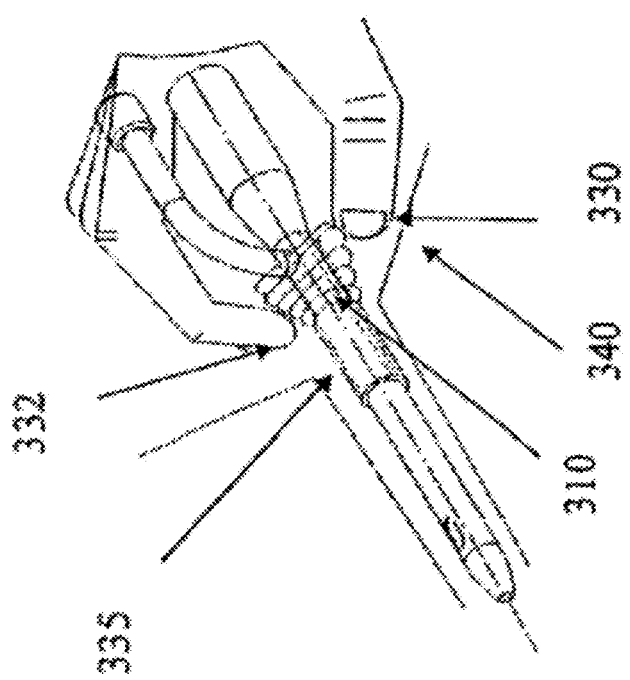

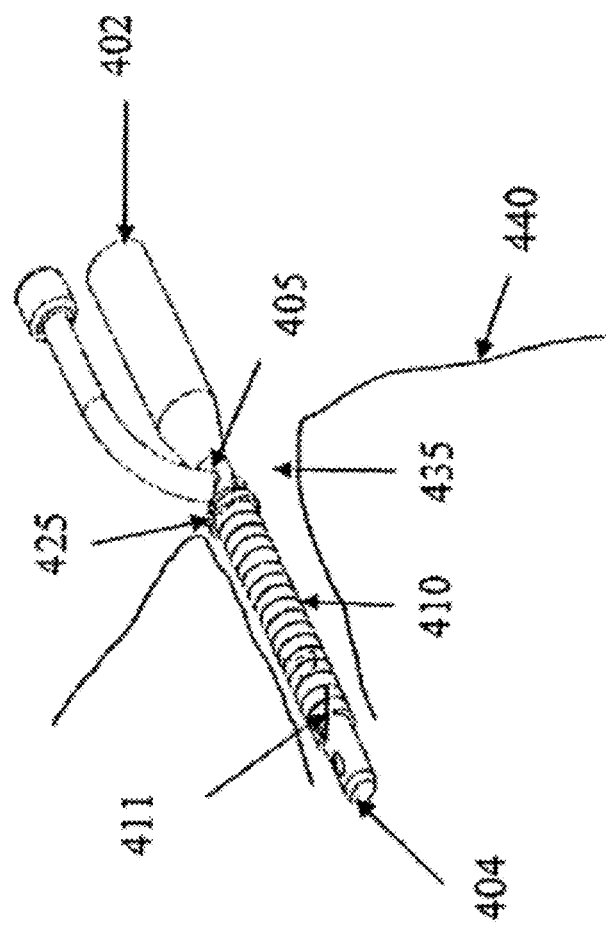

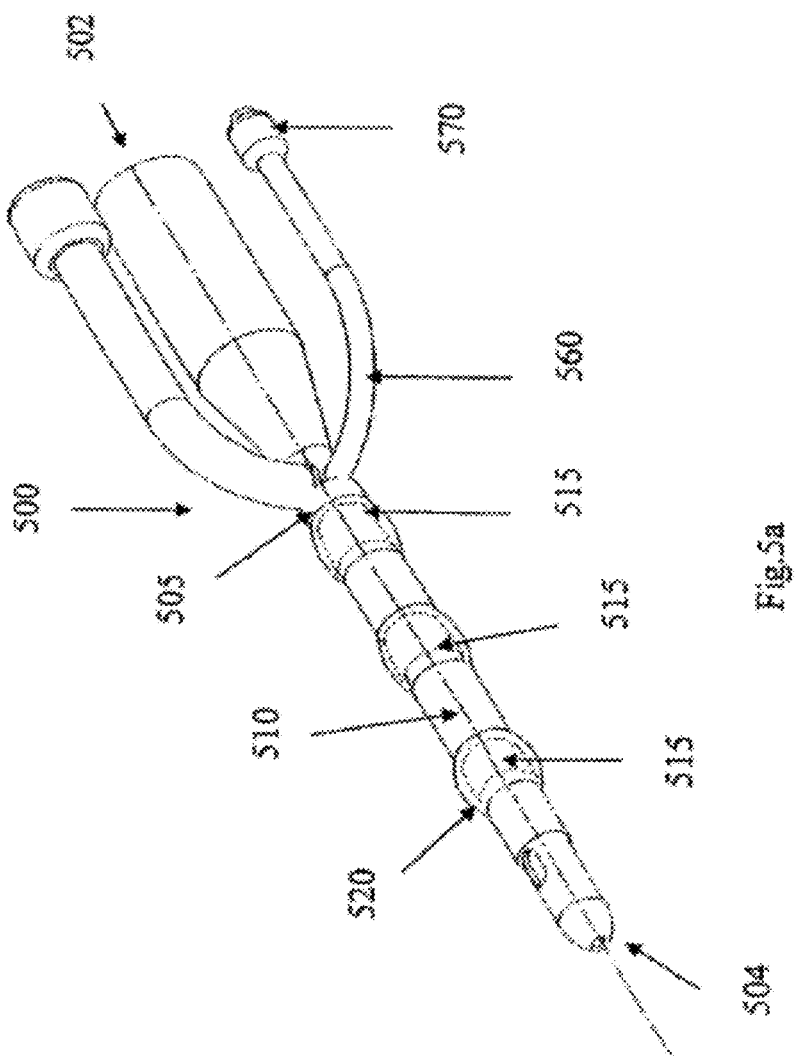

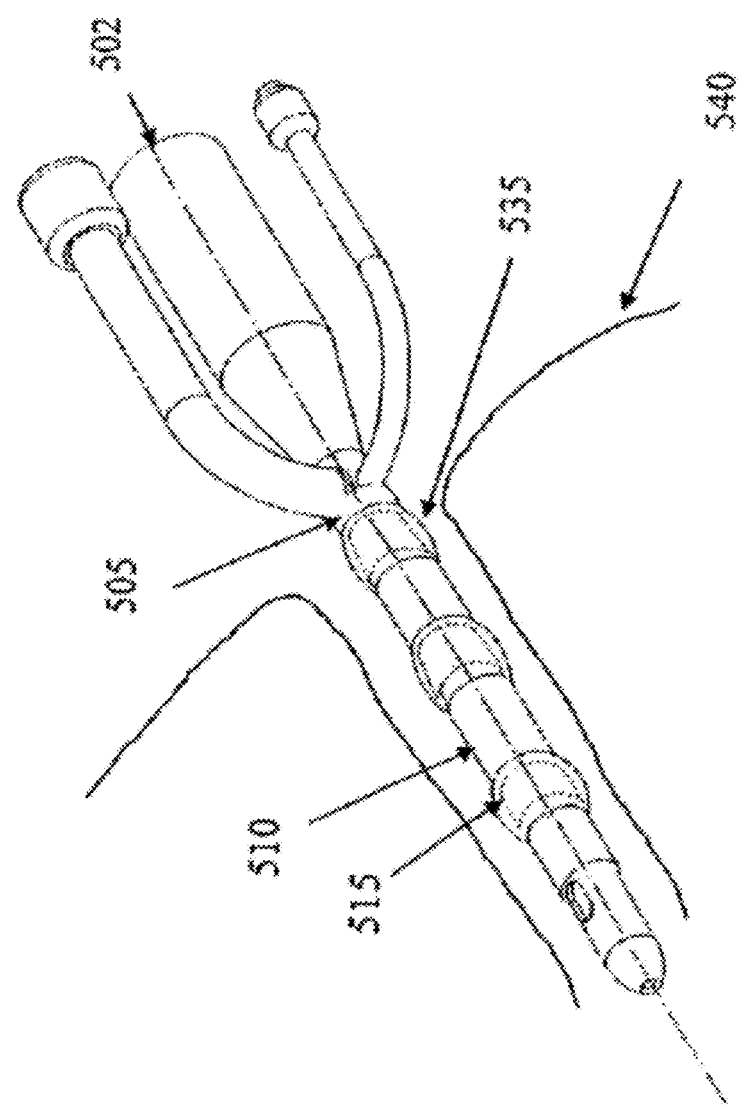

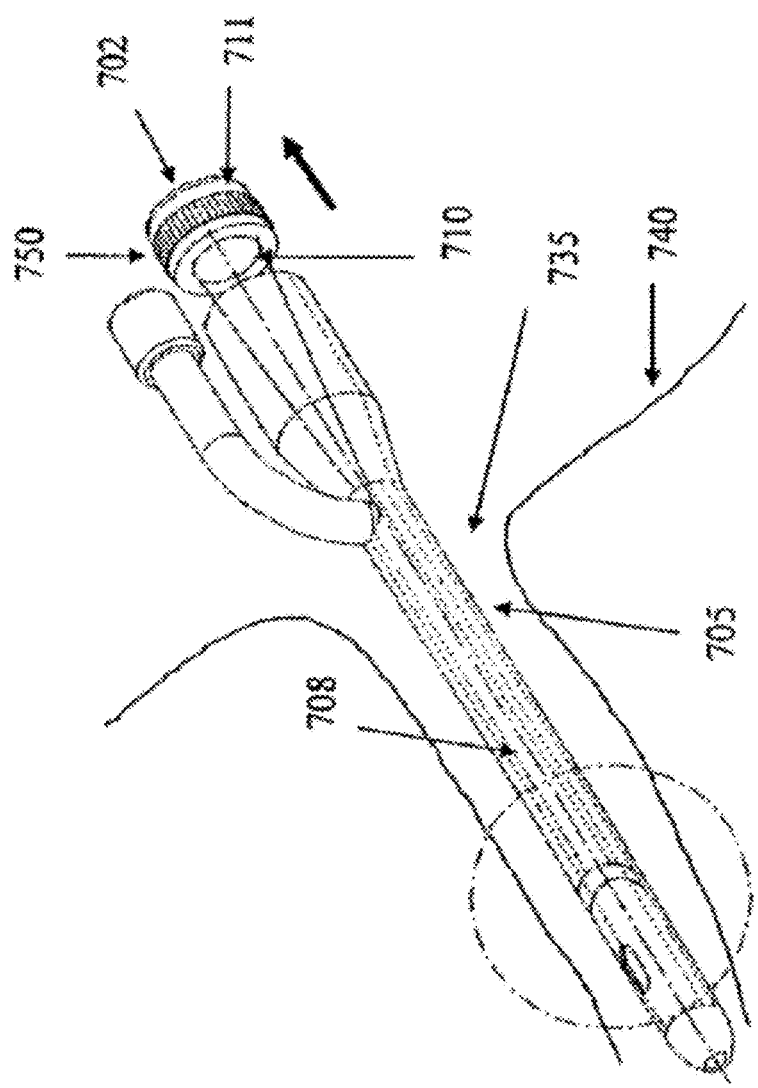

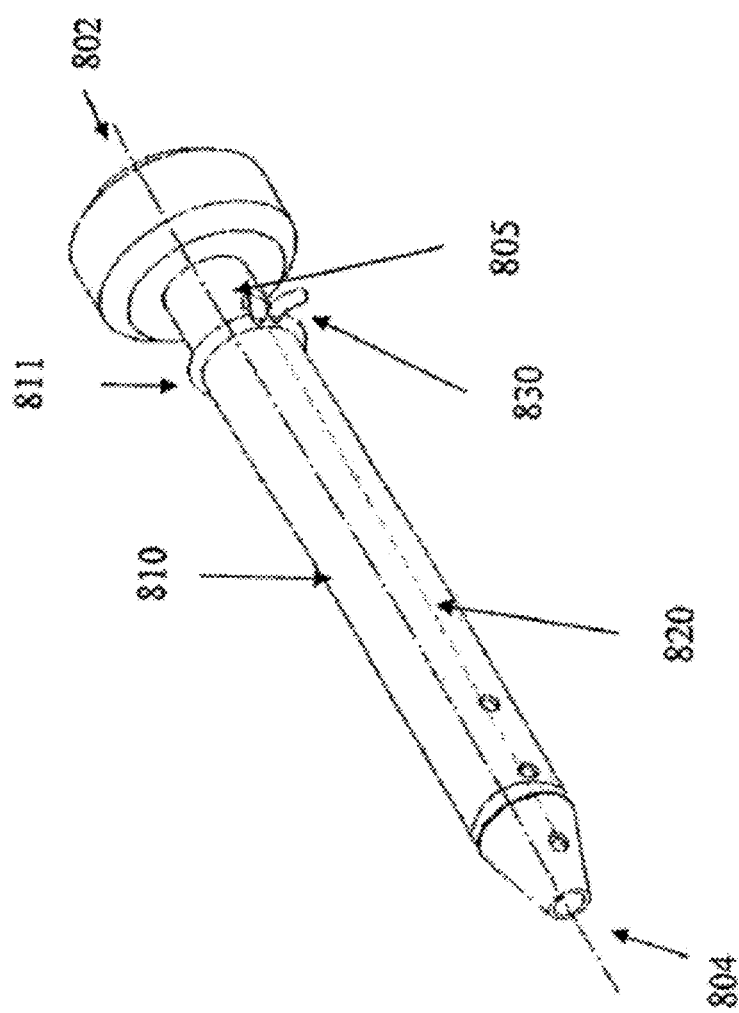

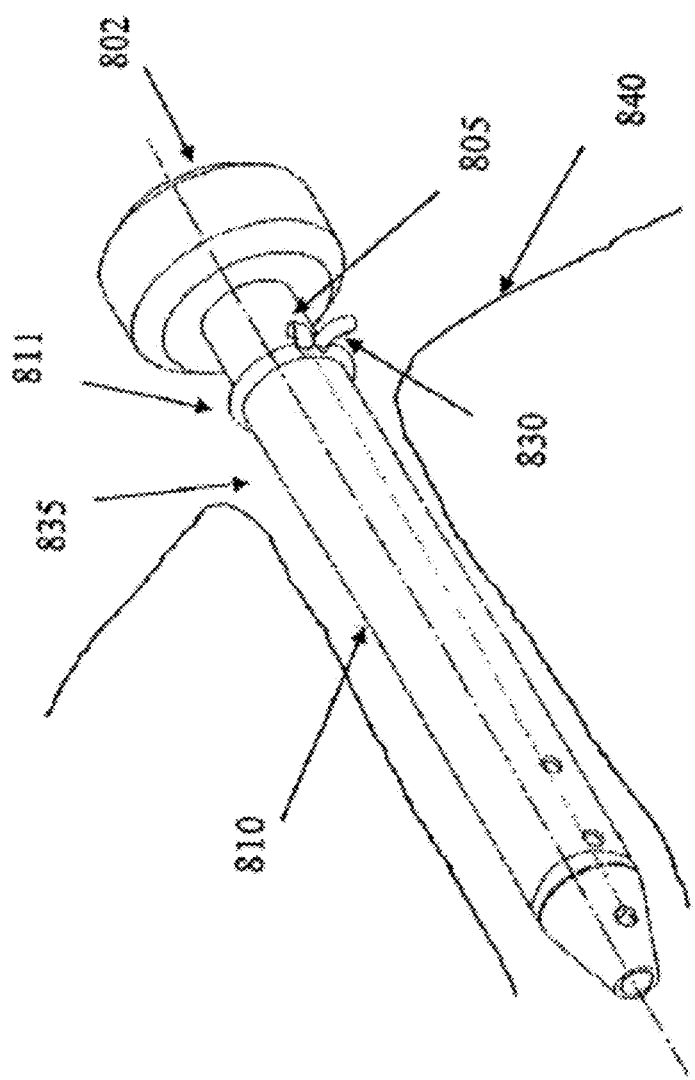

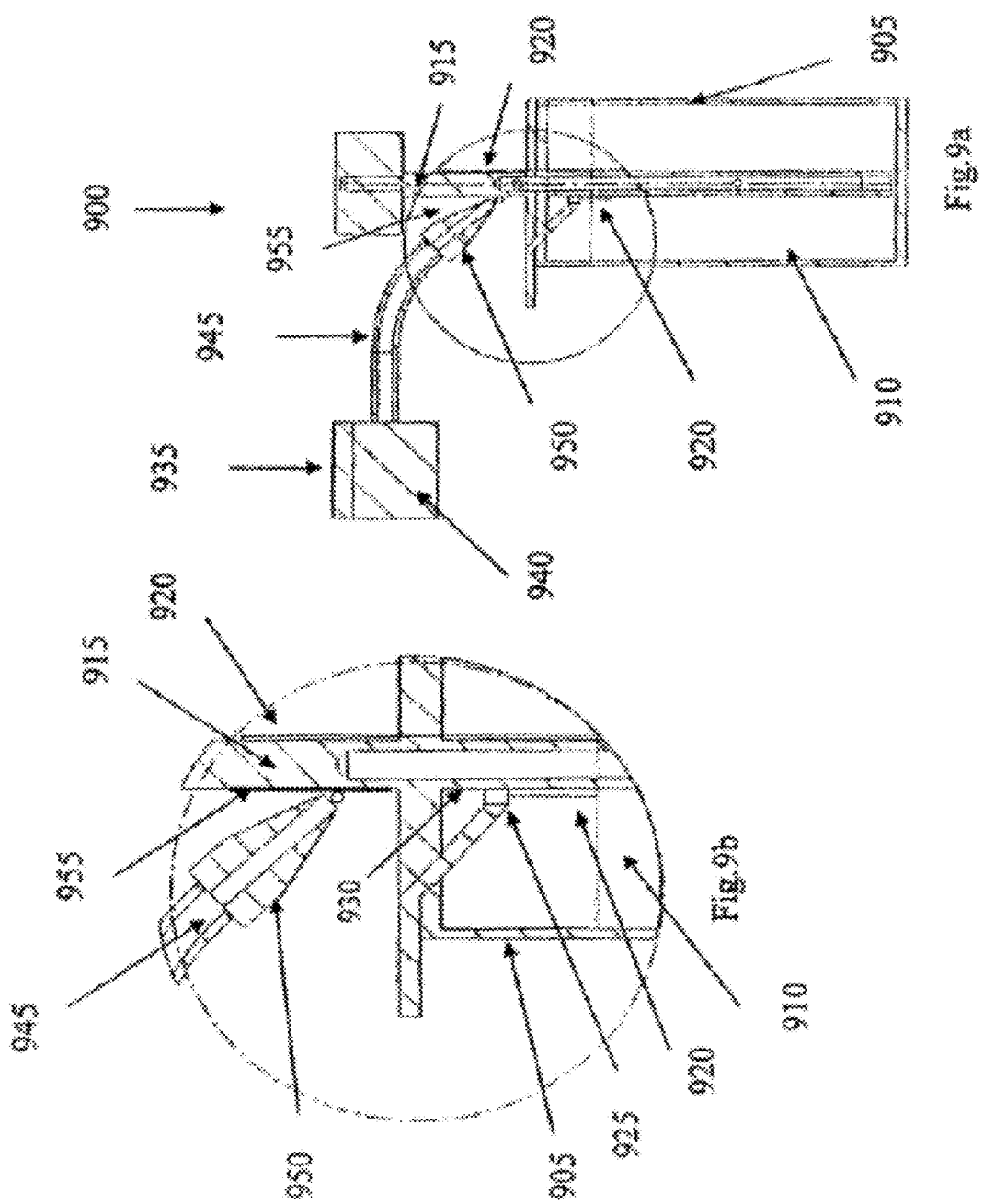

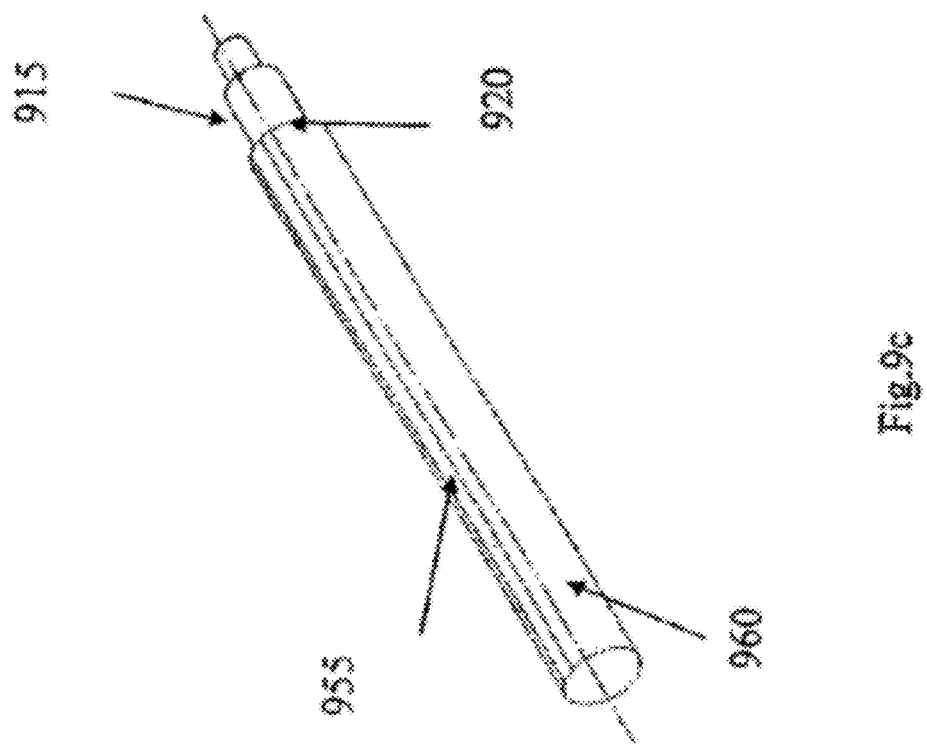

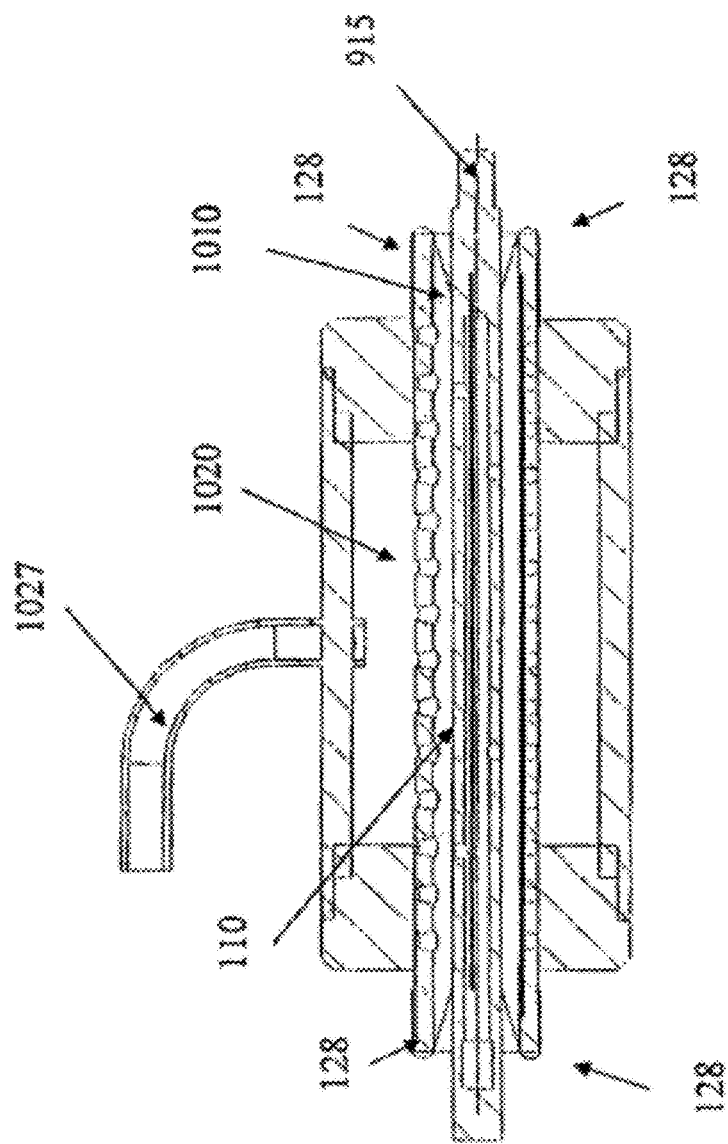

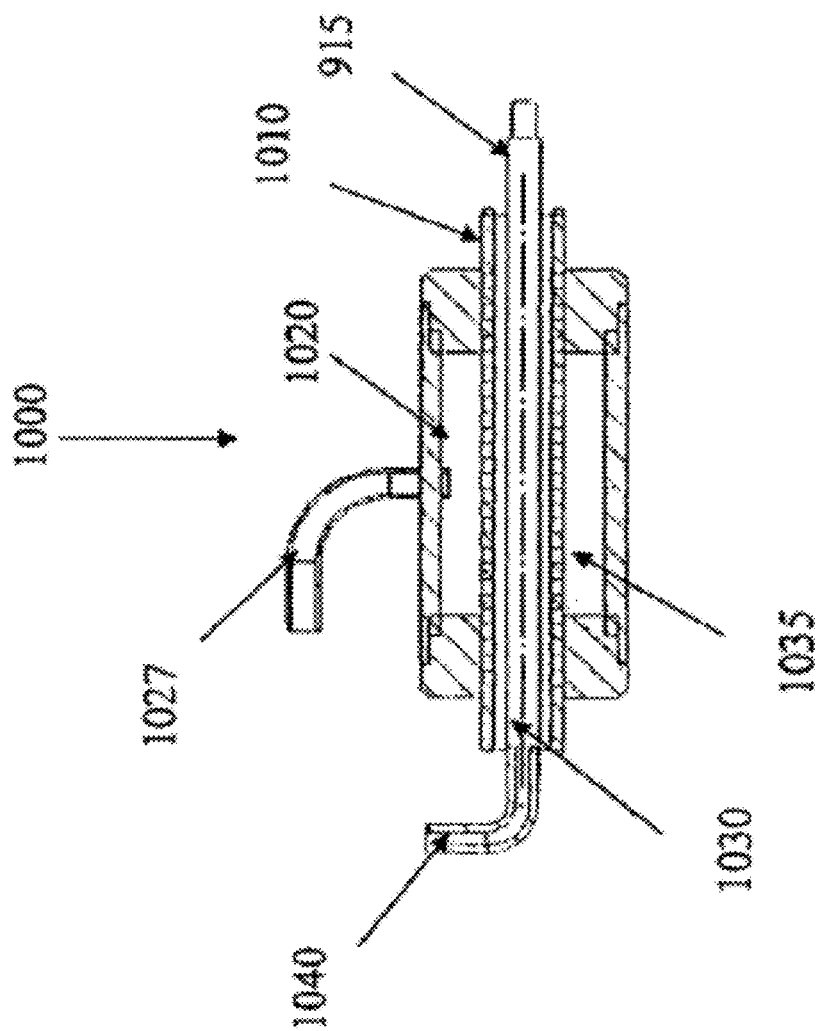

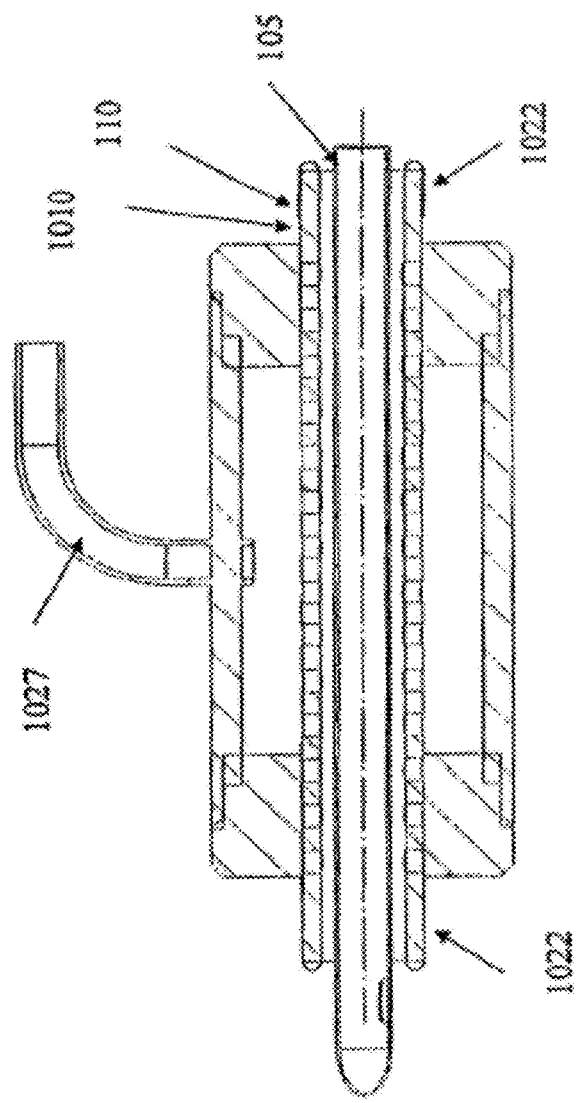

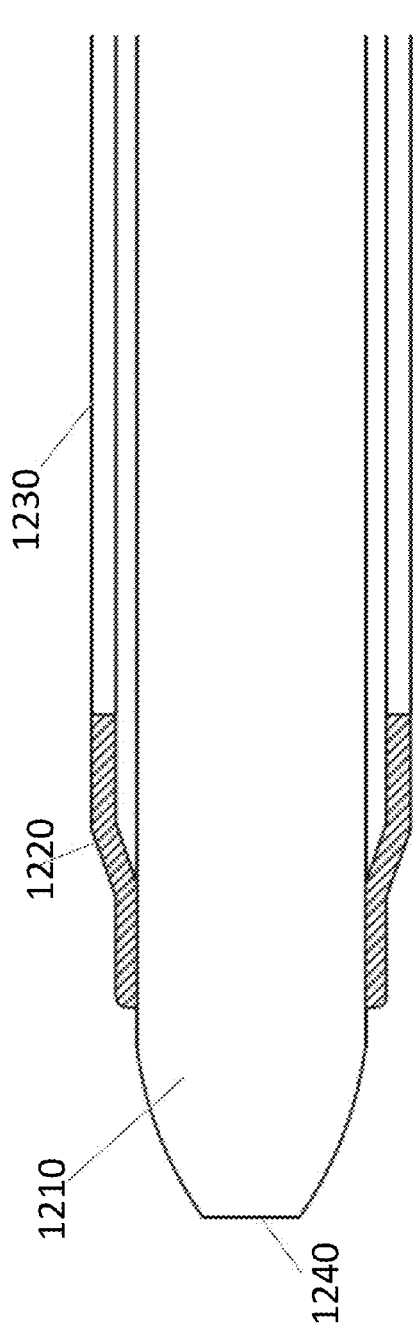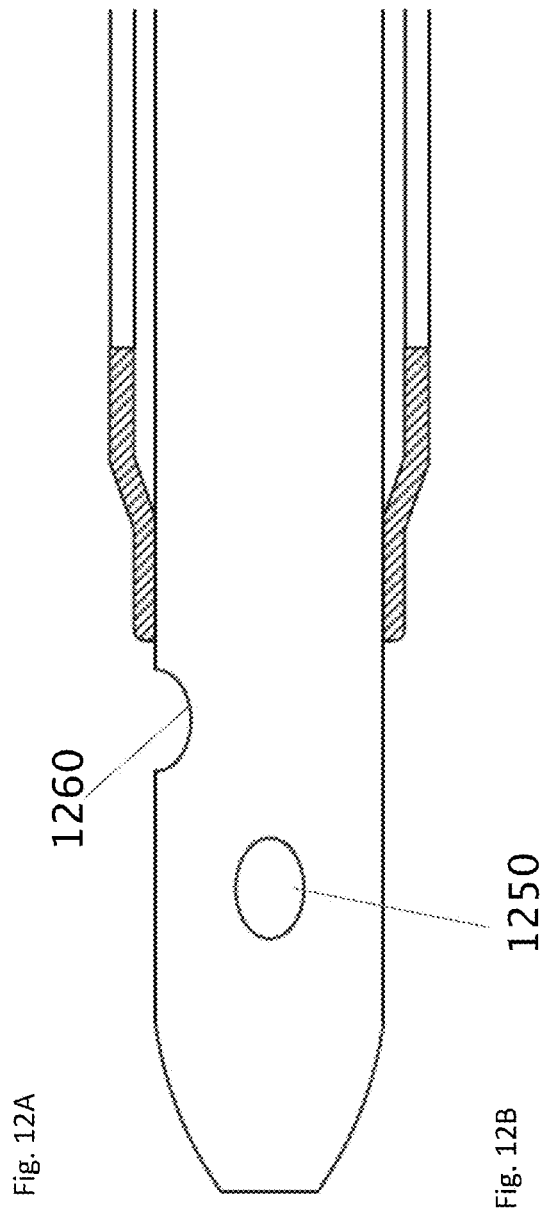
Fig. 12A
Fig. 12B

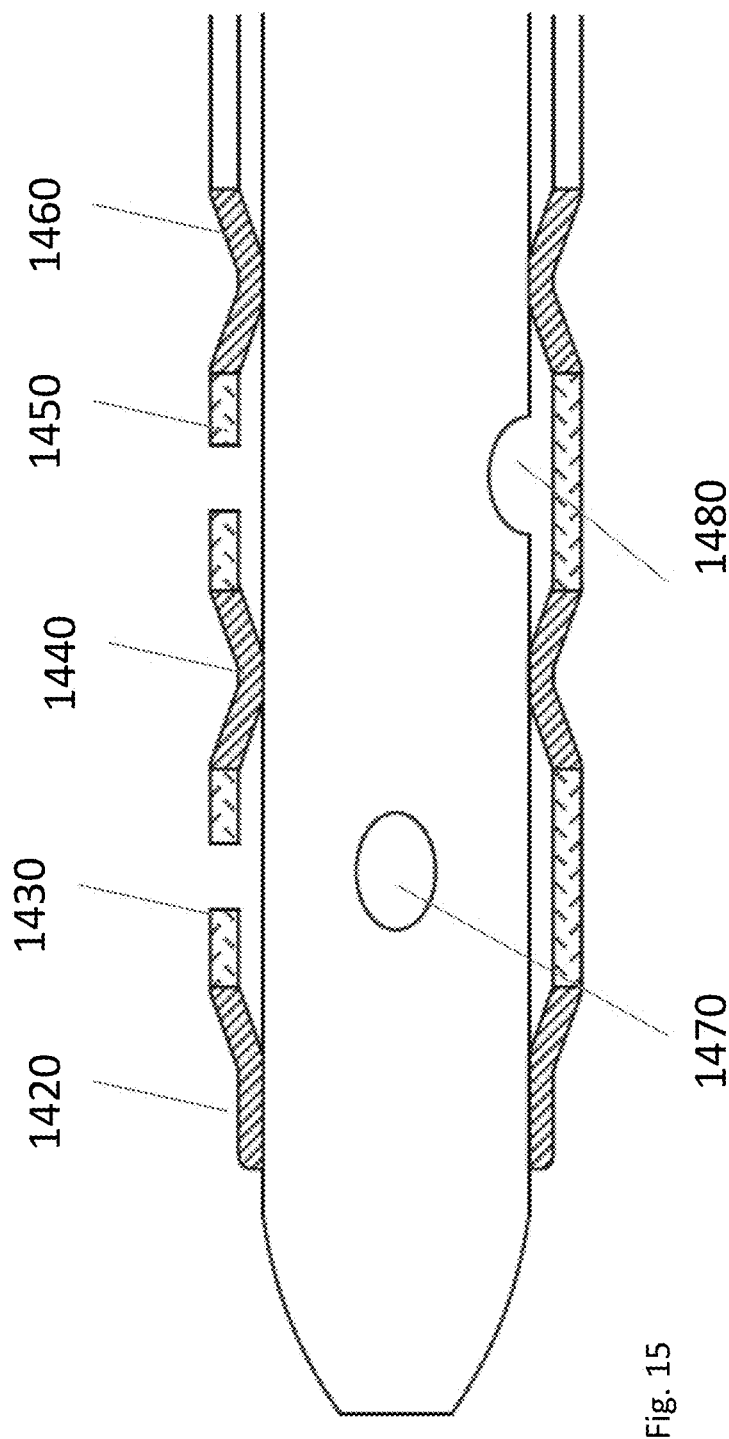

INDWELLING DEVICE

CROSS-REFERENCE TO RELATED PATENT APPLICATIONS

This application is a continuation in part (CIP) of U.S. patent application Ser. No. 12/591,952, filed Dec. 4, 2009, now allowed, which is incorporated herein by reference in its entirety.

FIELD OF THE INVENTION

The present invention is in the field of medical devices, and more specifically relates to indwelling medical devices.

BACKGROUND OF THE INVENTION

There are many medical devices that are inserted into the body and left indwelling for a prolonged period of time. These include, for example, various types of catheters, cannulae, drains, implants, stents, pacemakers, electrodes and other devices. Some of these devices, such as a urinary catheter, when in use, extend from the exterior of the body into the body interior, passing through an orifice on the body surface. The orifice may be a natural orifice (e.g. mouth, meatus, nostrils, etc.) or an artificial orifice (e.g. a hole formed in the skin by a surgical incision). Other indwelling devices, such as a pacemaker or stent, are completely enclosed inside the body during use. Accessing these devices typically requires surgical incising or other invasive approaches.

Although using indwelling devices is a common medical procedure, it is often limited due to formation of biofilm such as calcifications and other debris, and colonization of microorganisms, such as bacteria and fungi, on the surface of the device. This may cause inflammation and further infection around the device. The formation of biofilm and contamination is common with exposed indwelling devices, limiting the amount of time that they may be left in the body before having to be removed and possibly replaced with a new device.

Contamination of the device and tissues surrounding it may occur as the device is inserted into the body. For example, the end of a urethra closest to the meatus is naturally contaminated with various infectious agents, while the remainder of the urethra, nearer to the urinary bladder is normally sterile. During insertion of a catheter through the urethra to the urinary bladder, the catheter contacts infectious agents in the beginning of the urethra and spreads them up the urethra into the normally sterile portion and into the bladder. In order to reduce the spread of microorganisms up the urethra during insertion of a urinary catheter, it is known to first insert a hollow sheath into the beginning of the urethra that extends in the urethra to just beyond the contaminated region. A urinary catheter is then inserted through the sheath into the normally sterile part of the urethra, and into the bladder. The sheath thus intervenes between the catheter and the microorganisms in the infected part of the urethra, and thus decreases the chance of microorganisms spreading into the normally sterile portion of the urethra and into the bladder. After insertion of the catheter, the sheath is withdrawn from the body. Such sheaths are disclosed, for example, in U.S. Pat. No. 5,417,666.

Microorganisms may also migrate along an exposed indwelling device after its insertion along the outside surface of the device at its interface with the surrounding tissue. In order to inhibit the migration of microorganisms along the device, it is known to impregnate the device with antiseptic substances that are released from the catheter over time. A catheter designed to release antiseptic substances is disclosed, for example, in U.S. Pat. No. 3,598,127. Antiseptic impregnation, however, is not effective in the prevention of biofilm formation and is of very limited value in preventing infection due to the development of resistance among the microorganisms to the antibiotic.

SUMMARY OF THE INVENTION

It has now been found that it is possible to prevent the build-up of biofilm on the surfaces of indwelling medical devices by means of providing removable covers. By means of this arrangement, biofilm components become deposited on the surface of a cover instead of on the surface of the medical device itself. This cover may then be removed without disturbing the positioning or functioning of the indwelling device to which said cover was attached, thereby removing the built-up biofilm from the region of the device, and from the body. The act of removing the cover exposes either a further cover, enabling the removal process to be repeated, or, the external surface of the indwelling device itself. Unexpectedly, the inventors have found that it is possible to construct a covered device, such that the desired functioning thereof (for example the passage of fluids through a catheter or the mechanical dilatory action of a stent) is not affected or influenced by the presence of one or more covers on the surface of the device.

The term "biofilm", explained hereinabove, refers to the build-up of biologically-derived matter such as calcified material and other debris, as well as microorganisms, such as bacteria and fungi, on the surface of the device. This may cause inflammation and further infection around the device. In certain locations and in certain circumstances the biofilm and associated inflammatory processes may lead to undesirable blood clot formation.

The present invention is thus primarily directed to indwelling medical devices having an outer surface, at least a portion of which is protected by a manually detachable cover. During insertion, the cover is attached to the surface so as to prevent relative movement of the surface and the cover. This allows the integrity of the device and cover to be maintained during insertion. Once the covered device (e.g. catheter, stent, drain etc.) has been inserted into the desired operating location, said device may be manipulated or operated in the normal manner, without any hindrance or loss of functionality arising from the presence of the cover. At any time after insertion, the cover may be detached from the shaft and removed from the body, leaving the device in place. Removing the cover from the device removes the biofilm and contamination that has accumulated on the cover.

The cover is preferably made from non-allergic biocompatible materials such as natural rubber, silicone rubber, latex, woven metal mesh, parylene, polyvinylchloride, polyurethane, mylar, nylon and the like. The cover may be impermeable to body fluids or microorganisms. The cover may have a rough or smooth surface.

The covered device provided by the present invention may comprise any of the different types of indwelling medical devices known in the art. In particularly some embodiments, however, the medical device is selected from the group consisting of: (a) a catheter (e.g. a urinary catheter, venous catheter, arterial catheter dialysis catheter); (b) a cannula; (c) a drain; (d) a stent; (e) a pacemaker; and (f) an electrode.

The medical device may have a single or multiple lumens,
  each lumen may have an hole at the distal end and/or at
  least one hole along its shaft, for example venous multi
  lumen catheter with distal hole and side holes that may corresponding to different lumens. Another example is a single lumen drain with an opening at the distal end and side holes.

The present invention discloses a medical device for insertion into a body. The device having at least one surface covered by and attached to at least one detachable cover and at least one surface hole, the cover being detachable from the surface and removed from the body any time after the device has been inserted in the body.

The cover and the device are inserted in the body as a united device, such as the cover encapsulate and seals the medical device and the cover can be detached and pulled off the device which remains in the body, where the device cannot be pulled out from the cover while the cover remains within the body.

The covers may include at least one sealing element for preventing ingress of fluids between the cover and at least part of the medical device.

The cover and the at least one sealing element, encapsulate the medical device though it's length, overlapping at least one surface hole.

The cover and the at least one sealing element are designed to isolate at least one hole from at least another holes, while enabling free passage through it, in at least partial time period in which the medical device is within the body;

The presence of said cover does not prevent the device from fulfilling its intended function, and wherein said medical device is selected from the group consisting of: (a) a catheter; (b) a cannula; (c) a drain; (d) a stent; (e) a pacemaker; and (f) an electrode.

According to some embodiments of the present invention the seal element covers partial surface of the device in which the at least one surface hole is located and includes at least one seal hole, wherein each seal hole overlaps at least one surface hole and is located over at least one surface hole of the medical device.

According to some embodiments of the present invention, the seal element covers partial surface of the device in which the at least one surface hole is located and parts of the seal element is designed to include plurality of small holes or have a net structure.

According to some embodiments of the present invention, the cover integrates more than one seal element, where each seal element is located between two cover element and isolates the at least one surface hole, where each cover part corresponds to different surface hole.

According to some embodiments of the present invention the at least one cover element has at least one cover hole corresponding to at least one surface hole According to some embodiments of the present invention, the at least each cover is designed to include plurality of small holes or a net structure.

According to some embodiments of the present invention the seal element covers a partial surface of the device where the at least one hole is located, wherein the cover can be pulled out at least partially, such as, at least part of the surface in which one hole is located is exposed and the other parts of medical device surface may be remained covered.

According to some embodiments of the present invention the sealing element is formed from a material selected from the group consisting of: (a) rubber; (b) silicone rubber; (c) polyvinylchloride; (d) latex; (e) woven metal mesh; parylene; (g) polyurethane; (h) mylar; and (i) nylon According to some embodiments of the present invention the device is a urinary catheter.

According to some embodiments of the present invention the device is a venous catheter or arterial catheter.

According to some embodiments of the present invention the device is drain canola or electrode.

According to some embodiments of the present invention, the device is a dialysis catheter.

According to some embodiments of the present invention the device include a stack of at least two sequentially detachable covers, each cover being detachable either from the surface of the device or from the adjacent cover, and removed from the body while the device is within the body.

According to some embodiments of the present invention the cover is formed from a material selected from the group consisting of: (a) rubber; (b) silicone rubber; (c) polyvinylchloride; (d) latex; (e) woven metal mesh; parylene; (g) polyurethane; (h) mylar; and (i) nylon.

According to some embodiments of the present invention the cover or sealing element are formed from a biocompatible material.

According to some embodiments of the present invention, the cover or the sealing element is formed from a non-allergenic material.

According to some embodiments of the present invention, the cover is impenetrable to microorganisms.

According to some embodiments of the present invention, the cover is impenetrable to water.

According to some embodiments of the present invention the cover stores and releases a substance.

According to some embodiments of the present invention the substance is an anti-microbial or anti-fungal compound.

According to some embodiments of the present invention the, sealing element is made of polyurethane.

All the above and other characteristics and advantages of the present invention will be further understood from the following illustrative and non-limitative examples of some embodiments thereof.

BRIEF DESCRIPTION OF THE DRAWINGS

In order to understand the invention and to see how it may be carried out in practice, some embodiments will now be described, by way of non-limiting examples only, with reference to the accompanying drawings, in which:

FIGS. 3a-3d show an indwelling device having a rollable cover in accordance with another embodiment of the invention;

FIGS. 5a-5e show an indwelling device having a cover attached with internal balloons in accordance with another embodiment of the invention;

FIGS. 7a and 7b show an indwelling device having a cover attached on an inner surface;

FIGS. 8a-8d show an indwelling device having a tearable cover in accordance with another embodiment of the invention;

FIGS. 9a-9c show a system for preparing a cover on a mandrel in accordance with one embodiment of the invention; and FIGS. 10a-10h show a system for transferring a cover from a mandrel onto a device.

FIG. 12a illustrates a medical device with one hole having a cover attached to its outer surface with a sealing element according to some embodiments of the present invention;

FIG. 12b illustrates a medical device with more than one hole having a cover attached to its outer surface with a sealing element according to some embodiments of the present invention;

FIG. 15 illustrates a medical device with more than one hole having a cover attached to its outer surface with more than one sealing element having holes according to some embodiments of the present invention;

DETAILED DESCRIPTION OF EMBODIMENTS OF THE INVENTION

The invention will now be described by non-limiting embodiments. For the sake of clarity, the invention is exemplified by devices having a slender shaft such as catheters, cannulae, and drains. This is by way of example only, however, and the invention is not limited to such devices. Other devices having detachable covers are included within the scope of the invention, such as implants, stents, and pacemakers.

First Embodiment

Figure 1A:
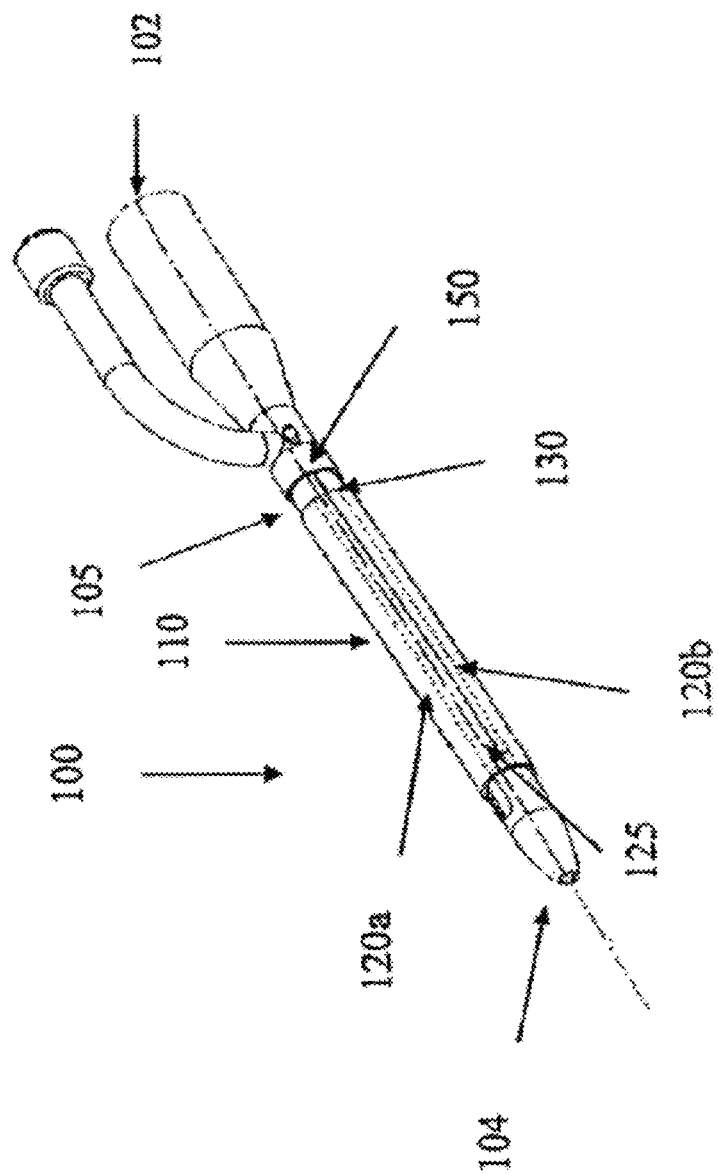
FIGS. 1a-1d show an indwelling device having a tearable cover in accordance with one embodiment of the invention.

FIG. 1a shows an indwelling device 100 in accordance with a first embodiment of the invention. The device 100 has a proximal end 102, a distal end 104, and a cylindrical shaft 105 that may be solid or hollow. The shaft 105 is contained in an outer cover 110 having the general shape of a thin cylindrical shell. The outer cover 110 is formed from a biocompatible, elastic material, such as latex, that was stretched over the shaft 105, and allowed to contract on the shaft 105. The outer cover 110 is reversibly attached to the shaft 105 by circumferential elastic forces in the outer cover 110 that are exerted on the shaft 105. This prevents slipping of the outer cover 110 over the shaft 105 during insertion of the device 100 into the body, and maintains the outer cover 110 on the shaft 105 after insertion.

The outer cover 110 is formed from two materials. The first material is used to form the cover except in a narrow strip 125 that is formed from a second material. The two materials are joined at two parallel seams 120a and 120b extending along the length of the outer cover 110. The strip of 125 formed from the second material preferably extends circumferentially for less than one quarter of the circumference of the outer cover 110. The first material has a relatively high tear stress, for example, a silicone rubber having a tear stress of 25 to 50 kN/M. The second material is a material having a relatively low tear stress, such as a silicone rubber with a tear stress of less than 5 kN/M. The preparation of silicone rubbers and other materials having a particular tear stress are known in the art.

Figure 6:
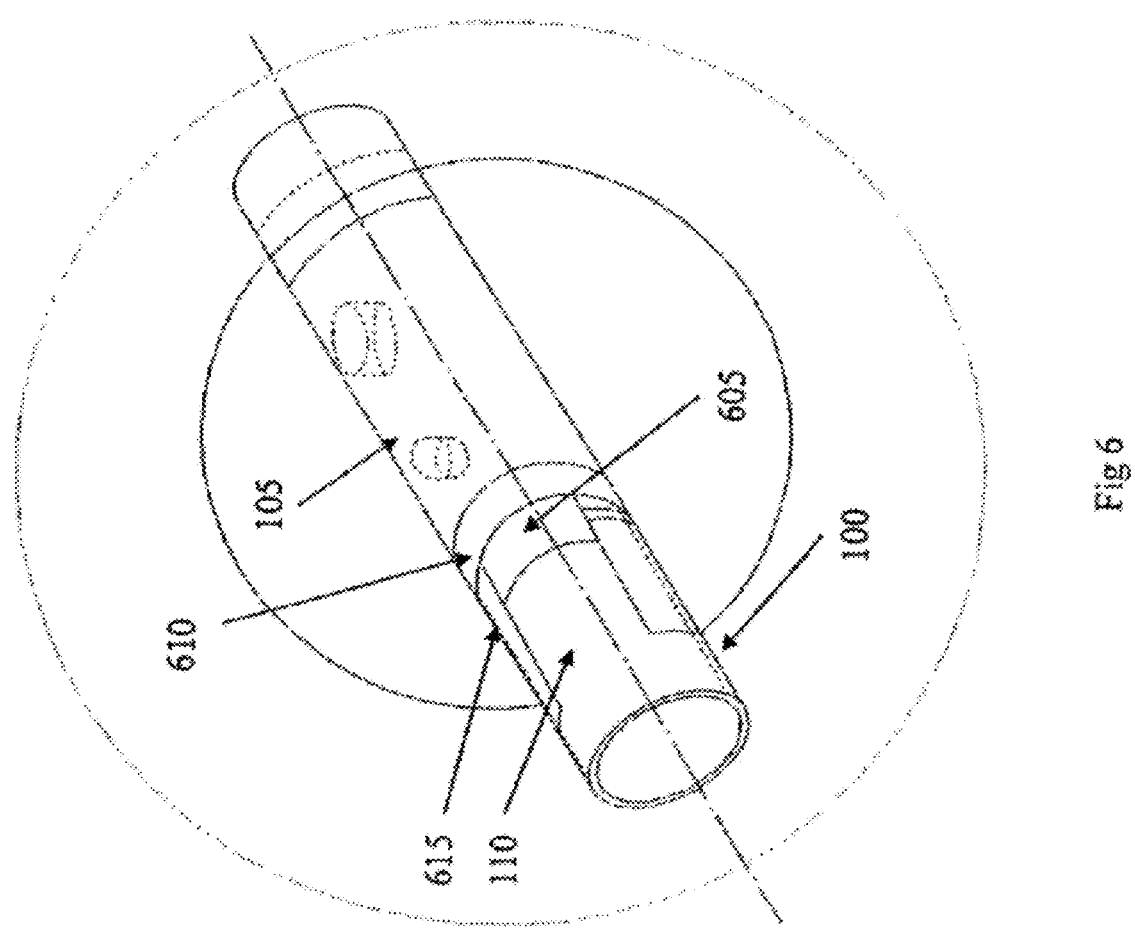
FIG. 6 shows use of a clamp securing the distal end of a cover to a surface.

Between the shaft 105 and the outer cover 110 is a cord 130. The cord is attached at one of its ends to the distal end of the strip 125. At its other end, the cord extends beyond the proximal end of the coating. A ring 150 holds the end of cord 130 on the shaft 105. As shown in FIG. 6, the device 100 may optionally comprise a distally located annular clamp 610 that secures the distal end of the outer cover 110 to the shaft 105 and prevents debris from accumulating under the distal end of the outer cover 110 during insertion.

Figure 1B:
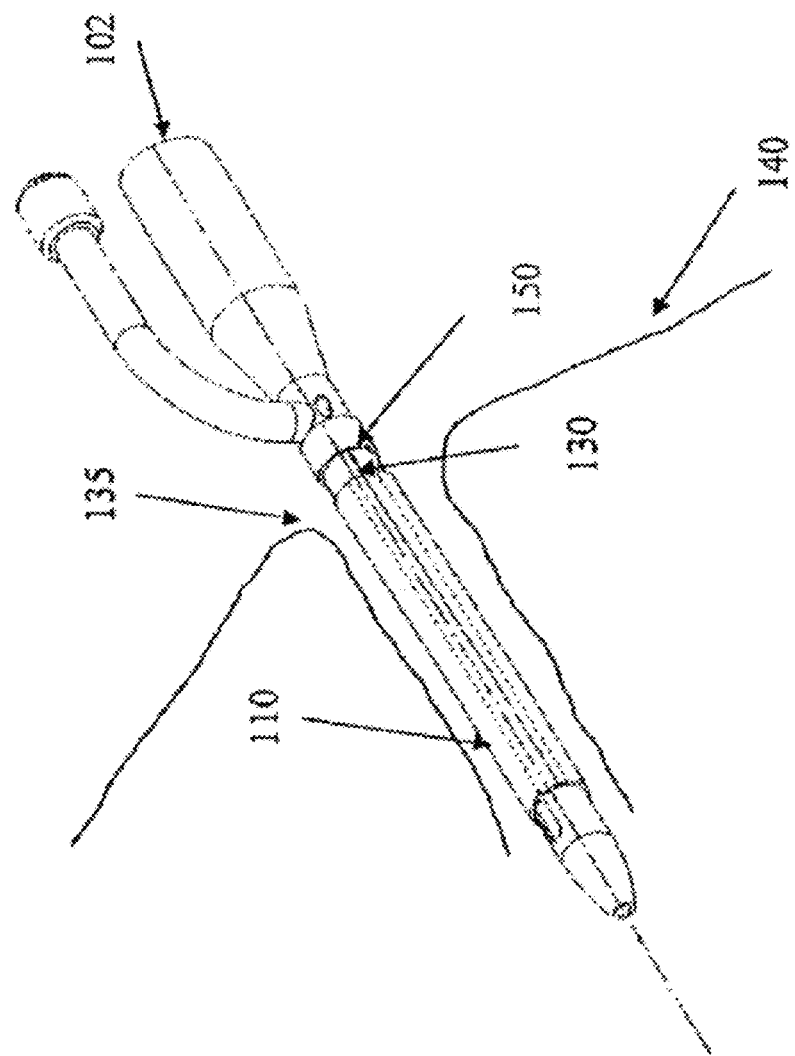

FIG. 1b shows the catheter of FIG. 1a after insertion into the body. The catheter 100 was inserted into the body through a hole 135 on the body surface 140. The hole 135 may be a natural hole on the body surface (e.g. mouth, meatus, nostrils, etc.) or an artificial hole (e.g. a hole formed in the skin by a surgical incision). After insertion, the proximal end of the cord 130 extends through the hole 135 and is exposed on the body surface. This is by way of example only, and the device may in use be completely enclosed within the body. In this case, a surgical cut is made in order to access the proximal end of the cord 130. Relative movement of the shaft 105 and the outer cover 110 is prevented during insertion due to the circumferential elastic forces of the outer cover 110 on the shaft 105.

Figure 1C:
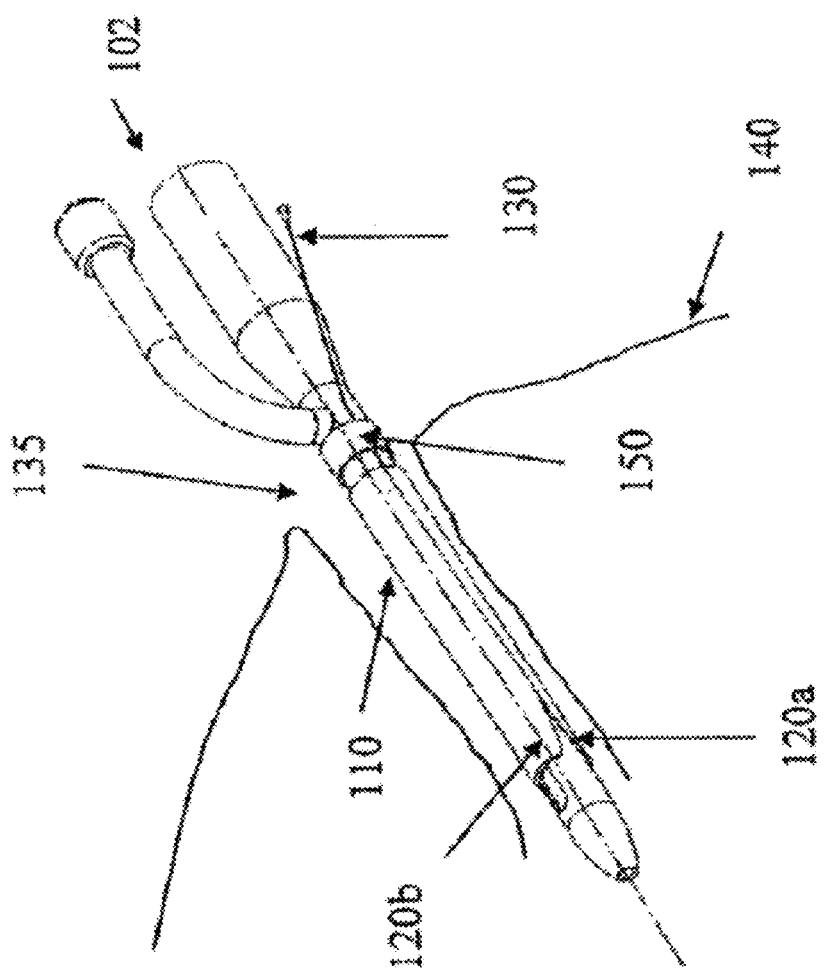
Figure 1D:
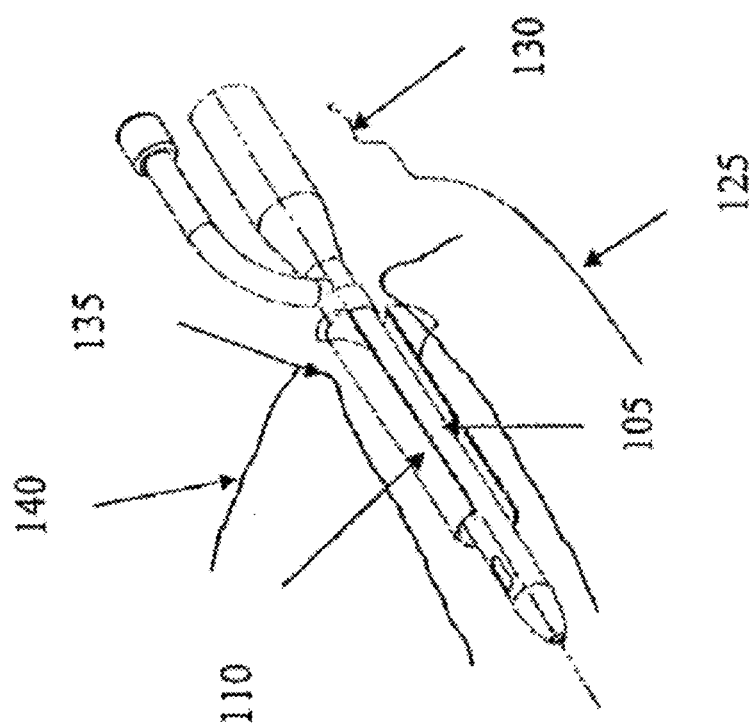

At any time after insertion, the outer cover 110 may be detached from the device 100 by removing the ring 150 and pulling the distal end of the cord 130. Pulling the cord 130 away from the body draws the distal end of the strip 125 into the space between the coating 110 and the shaft 105, tearing the distal ends of the seams 120a and 120b. (FIG. 1c). As the cord 130 continues to be pulled, tearing of the seams 120a and 120b progresses from the distal end towards the proximal end, until the entire strip 125 has been detached from the rest of the layer 110 and removed from the body (FIG. 1d). This detaches the outer cover 110 from the shaft 105. The proximal end of the torn outer cover 110 may now be grasped and manually removed from the body leaving the device 100 in place. If after removal of the outer cover 110, a new detachable outer cover (not shown) becomes exposed on the shaft, the newly exposed detachable layer may later on be removed from the device.

FIG. 9 shows a system, generally indicated by 900, for preparing the cover 110. A reservoir 905 contains a first liquid suspension 910 for preparing the first material in the cover 110. A cylindrical mandrel 915 is used upon which the cover 110 is to be formed. The mandrel 915 has a diameter corresponding to the inner diameter of the cover 110. A length of the mandrel 915 is submerged in the suspension 910. As the mandrel 915 is withdrawn from the suspension 910, a layer 920 of the first material coating the mandrel is formed.

A wiper blade 925 is used to remove a portion of the coating 920 as the mandrel 915 is withdrawn from the suspension 910. Above the wiper 925, a narrow strip 930 of the surface of the mandrel 915 thus becomes exposed.

A second reservoir 935 contains a second suspension 940 that is used to form the second material of the coating 110. The second suspension 940 is delivered to the surface of the mandrel 915 through a tube 945. A nozzle 950 applies the second suspension to the exposed strip 930 of the mandrel 915 surface, as the mandrel 915 is withdrawn from the first suspension 910. The second suspension 940 thus forms a coating 955 on the mandrel 915 in the exposed strip 930 created by the wiper 925.

FIG. 9c shows the mandrel 915 after having been removed from the reservoir 905. A cylindrical coating 960 has been formed on the mandrel 915. The coating consists of the first portion 920 formed by the first suspension 910 and the second portion 955 formed by the second suspension 940. The mandrel 915 is then placed in an oven in order to allow the coating to cure so as to form the cover 110. The first suspension 910 thus formed the first material of the cover, and the second suspension 940 formed the second material.

FIG. 10 shows a system, generally indicated by 1000, for transferring the cover 110 from the mandrel 915 to the shaft 105 of the device 100. The system 1000 is shown in plan view in FIG. 10a and in cross-section in FIG. 10b. The system 1000 has a housing 1005. A cylindrical tube 1010 passes through the housing 1005 and has a diameter configured to alternately receive the coated mandrel 915 and the shaft 105 of the device 100, as described below.

Figure 10A:
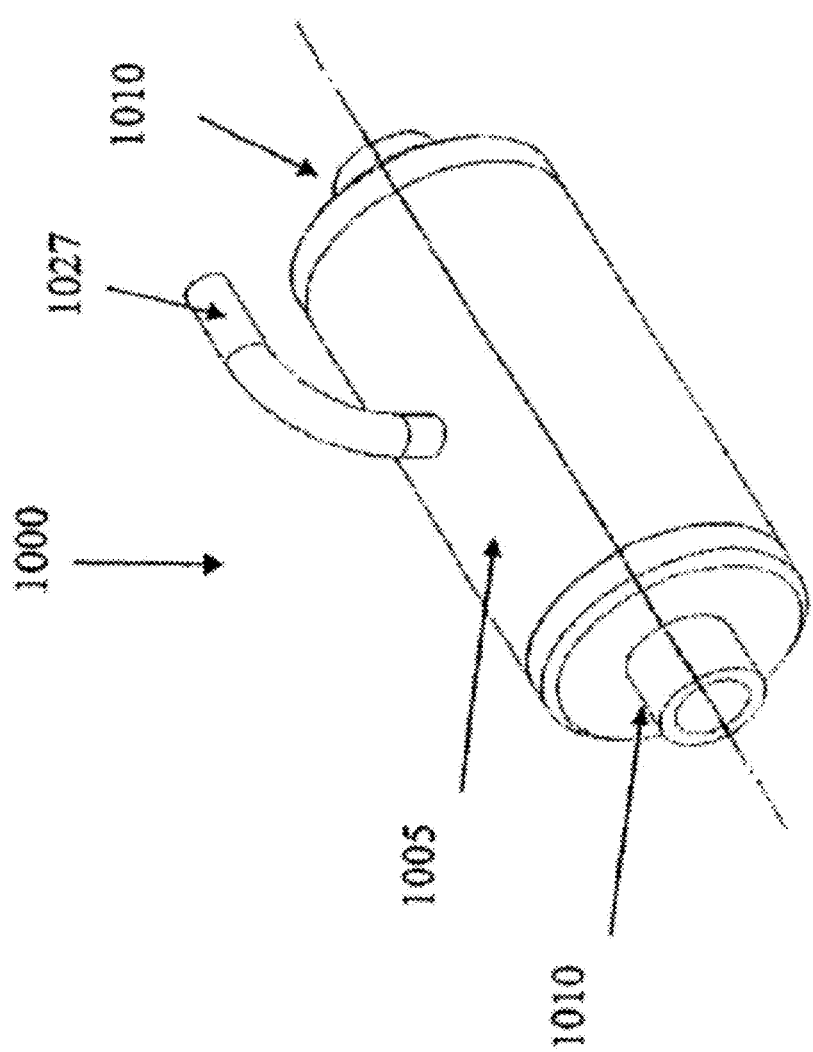
Figure 10B:
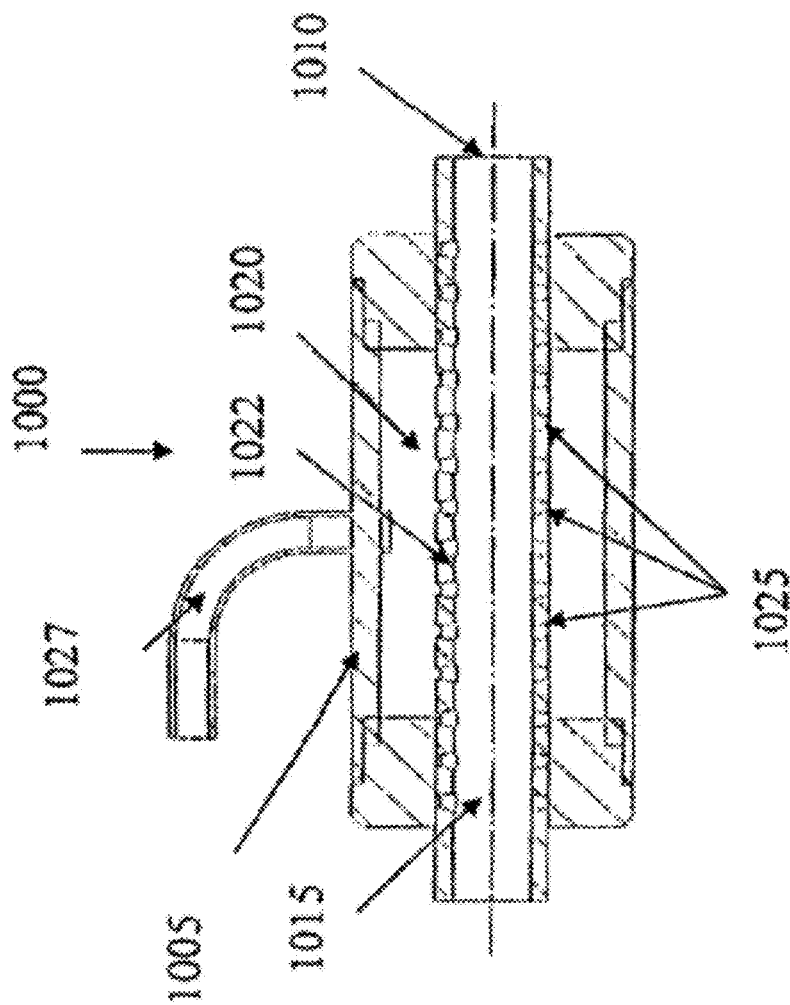

FIG. 10b shows the interior 1015 of the system 1000. A cylindrical space 1020 surrounds the cylinder 1010. The wall 1022 that is common to the space 1020 and the cylinder 1010 contains a plurality of pores 1025 allowing the flow of air between the interior 1015 of the cylinder 1010 and the space 1020. When the ends of the cylinder 1010 are sealed, as described below, the chambers 1015 and 1020 may be evacuated by removing air in the chambers through a tube 1027 that is connected to a source of negative pressure (not shown).

Figure 10C:
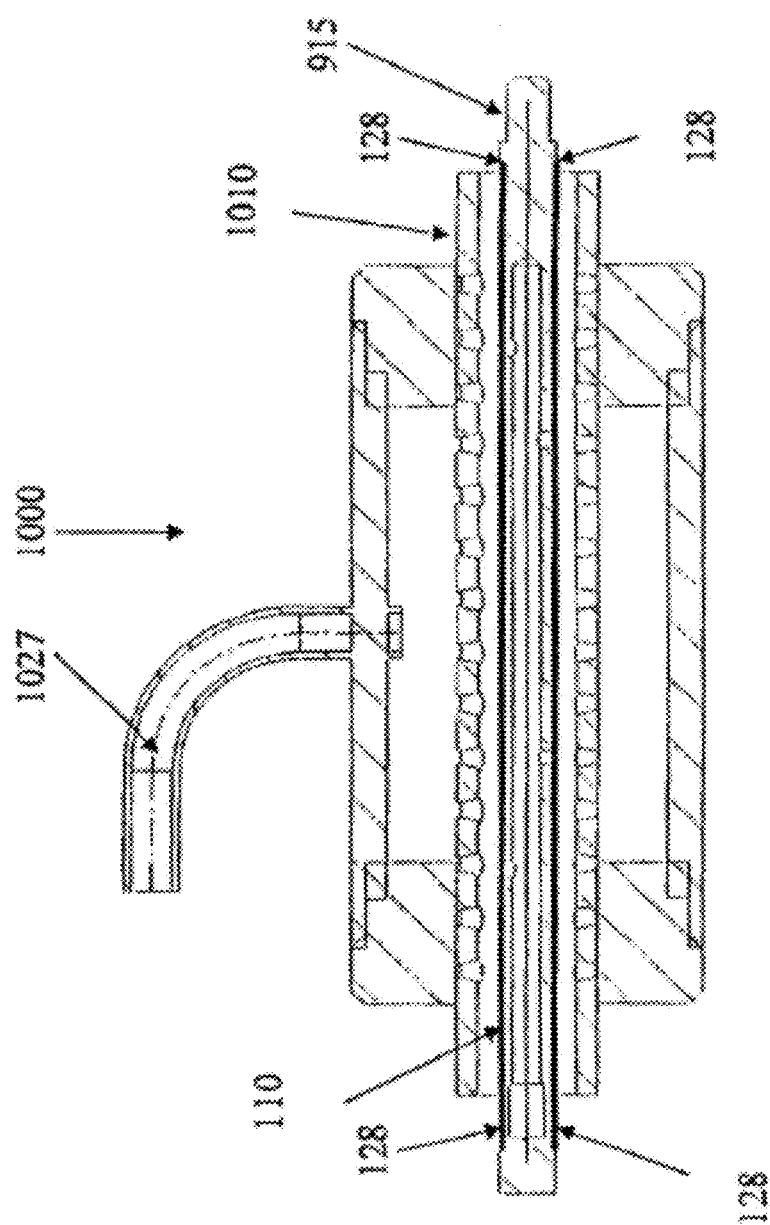

FIG. 10c shows the system 1000 after the mandrel 915 has been inserted into the cylindrical tube 1010. As described above, the mandrel 915 is contained in the cover 110 that is to be transferred from the mandrel 915 to the shaft 105 of the device 100.

Figure 10F:
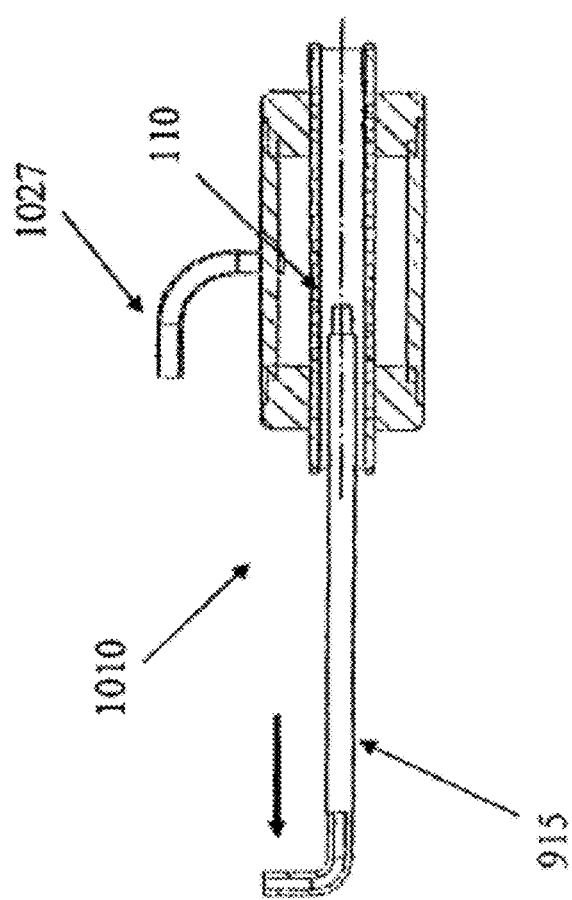

As shown in FIG. 10d, the ends 128 of the cover 110 are then rolled off the mandrel 915 and onto the ends of the tube 1010, thus sealing the ends of the cylinder 1010. The chamber 1020 is then evacuated causing the cover 110 to dissociate from the mandrel 915 and associate with the inner surface of the cylinder 1010, as shown in FIG. 10e. Dissociation of the cover 110 from the mandrel 915 may be enhanced if the mandrel is formed with a hollow core 1030 that is confluent with the exterior by pores 1035 in the wall of the mandrel 915, as shown in FIG. 10f. A source of positive pressure (not shown) is applied to the core 1030 by means of a tube 1040. The mandrel is then removed from the cylinder 1010 leaving the cover 110 mounted on the inner surface of the cylinder 1010, as shown in FIG. 10f.

Figure 10H:
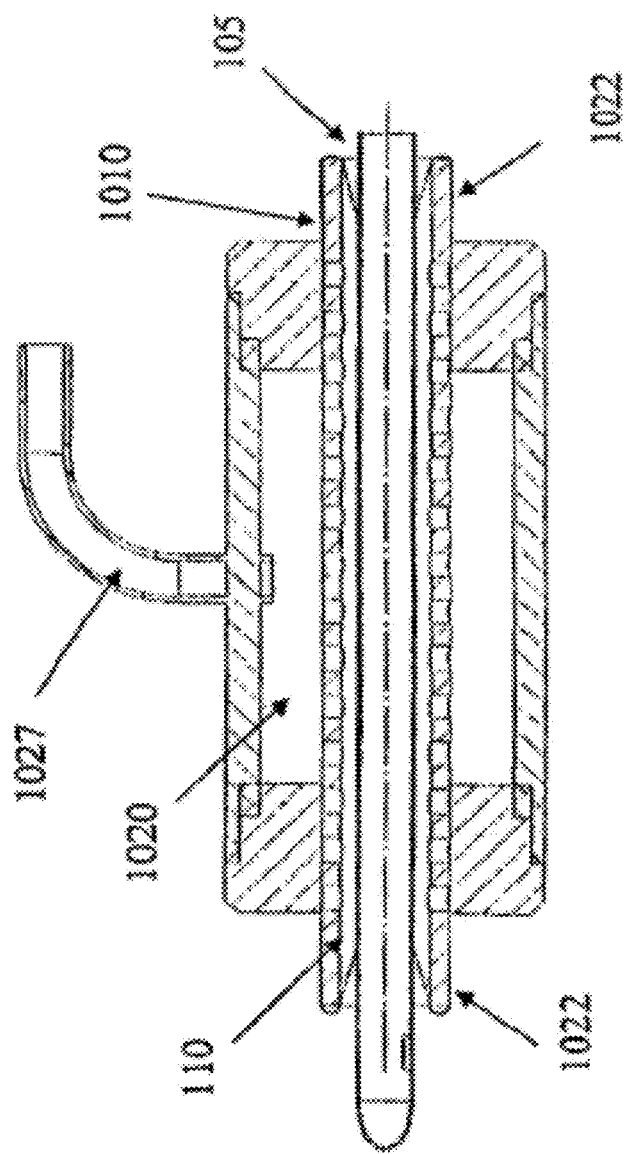

Now the shaft 105 of the device 100 is inserted into the cylinder 1010 as shown in FIG. 10g. The source of negative pressure is then disconnected from the tube 1027, causing the cover 110 to dissociate from the wall of the cylinder 1010 and associate with the shaft 105 of the device 100, as shown in FIG. 10h. The ends of the cover 110 are then unrolled from the cylinder 1010 onto the shaft 105, and the shaft 105 is removed from the interior of the cylinder 1010 with the cover 110 in place.

Second Embodiment

Figure 2:
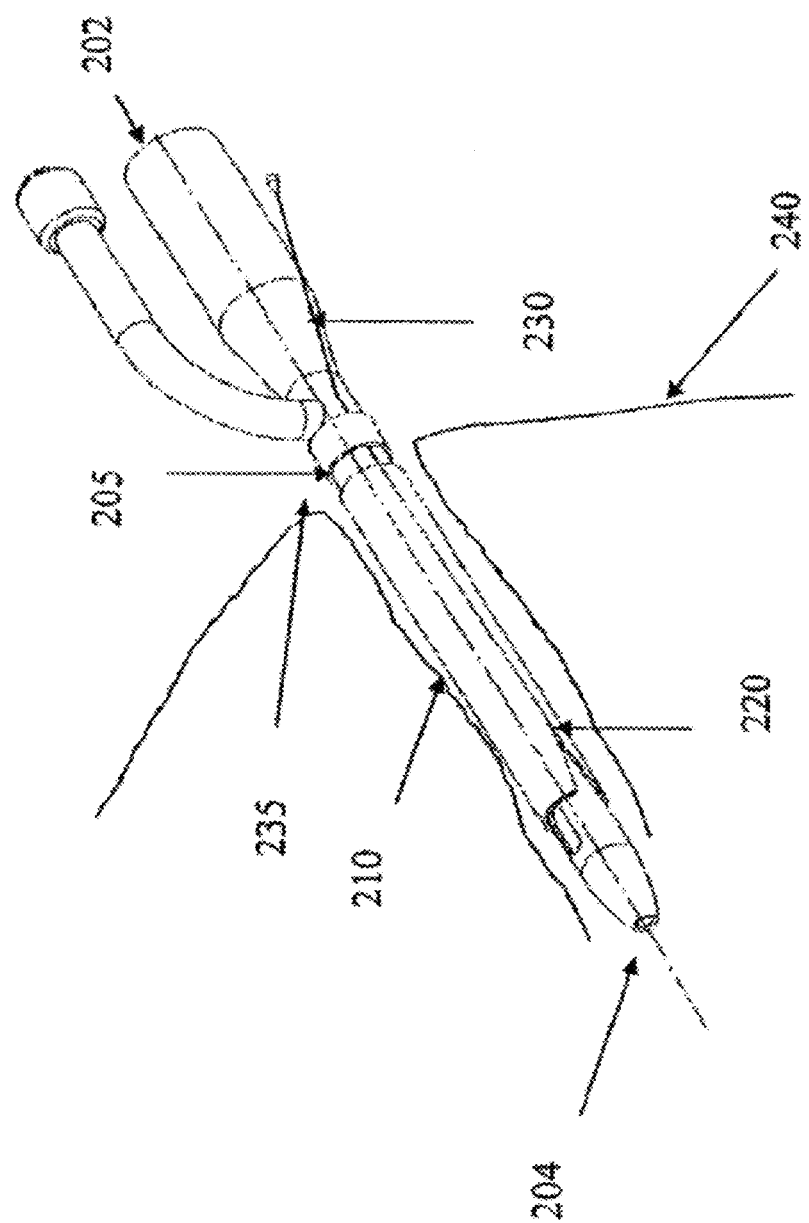
FIGS. 2a-2c show an indwelling device having a cutable cover in accordance with another embodiment of the invention.

FIG. 2a shows an indwelling device 200 in accordance with another embodiment of the invention. The device 200 has a proximal end 202, a distal end 204, and a cylindrical shaft 205 that may be solid or hollow. The shaft 205 is contained in an outer cover 210 having the general shape of a thin cylindrical shell. The outer cover 210 is formed from a biocompatible, elastic material, such as latex, that was stretched over the shaft 205, and allowed to contract on the shaft 205. The outer cover 210 is reversibly attached to the shaft 205 by circumferential elastic forces in the outer cover 210 that are exerted on the shaft 205. This prevents slipping of the outer cover 210 over the shaft 205 during insertion of the device 200 into the body, and maintains the outer cover 210 on the shaft 205 after insertion.

As shown in the insert FIG. 2a-I of FIG. 2a, the shaft has a longitudinal groove 215 that forms a track for a blade 220. The blade 220 is slidable along the groove 215. During insertion into the body, the blade 220 is positioned at the distal end of the groove 215. Between the shaft 205 and the outer cover 210 is a cord 230. The cord is attached at one of its ends to the blade 220. At its other end, the cord 215 extends beyond the proximal end of the coating.

FIG. 2b shows the device 200 after insertion into the body. The device 200 was inserted into the body through a hole 235 on the body surface 240. The hole 235 may be a natural hole on the body surface (e.g. mouth, meatus, nostrils, etc.) or an artificial hole (e.g. a hole formed in the skin by a surgical incision). After insertion, the proximal end of the cord 230 extends through the hole 235 and is exposed on the body surface. This is by way of example only, and the device may in use be completely enclosed within the body. In this case, a surgical cut is made in order to access the proximal end of the cord 230. Relative movement of the shaft 205 and the outer cover 210 is prevented during insertion due to the circumferential elastic forces of the outer cover 210 on the shaft 205.

At any time after insertion, the outer cover 210 may be detached from the device 200 by pulling the proximal end of the cord 230. Pulling the cord 230 away from the body draws the blade 220 towards the proximal end of the shaft 205 thus making a longitudinal cut 233 in the cover 210. (FIG. 2c). A guard 222 (FIG. 2a-I) on the blade prevents the blade from cutting any underlying covers. As the cord 230 continues to be pulled, cutting of the cover 210 progresses from the distal end towards the proximal end, until the cut extends along the entire length of the cover 210. This detaches the outer cover 210 from the shaft 205. The proximal end of the cut outer cover 210 may now be grasped and manually removed from the body leaving the device 200 in place. If after removal of the outer cover 210, a new detachable outer cover (not shown) becomes exposed on the shaft, the newly exposed detachable layer may later on be removed from the device.

Third Embodiment

FIG. 3a shows a device 300 in accordance with another embodiment of the invention. The device 300 has a proximal end 302, a distal end 304, and a cylindrical shaft 305. The shaft 305 is contained in an outer cover 310 having the general shape of a thin cylindrical shell. The outer cover 310 is formed from a biocompatible, elastic material, such as latex. The outer cover 310 was formed from an inner cylindrical shell 322 and an outer cylindrical shell 324. The inner and outer shells 322 and 324 are welded together at a first circular seam 326 at its distal end and a second circular seam 327 at its proximal end. The outer cover 310 was stretched over the shaft 305, and allowed to constrict on the shaft 305. The outer cover 310 is reversibly attached to the shaft 305 by circumferential elastic forces in the outer cover 310 that are exerted on the shaft 305. This prevents movement of the outer cover 310 relative to the shaft 305 during insertion of the device 300 and maintains the outer cover 310 on the shaft 305 after insertion.

FIG. 3b shows the device of FIG. 3a after insertion into the body. The catheter 300 was inserted into the body through a hole 335 on the body surface 340. The hole 335 may be a natural hole on the body surface (e.g. mouth, meatus, nostrils, etc.) or an artificial hole (e.g. a hole formed in the skin by a surgical incision). The proximal end of the outer cover 310 extends through the hole 335 and is exposed on the body surface. This is by way of example only, and the device may in use be completely enclosed within the body. In this case, a surgical cut is made in order to access the proximal end of the outer cover 310. Relative movement of the shaft 305 and the outer cover 310 is prevented during insertion due to the circumferential elastic forces of the outer cover 310 on the shaft 305.

At any time after insertion, the outer cover 310 may be detached from the device 300 by causing the outer cylindrical shell 324 to slide proximally over the inner cylindrical shell 322. As shown in FIG. 3c, this may be accomplished by placing a thumb 330 and an index finger 332 on the outer cylindrical shell 324 and urging the outer cylindrical shell 324 to slide proximally over the inner cylindrical shell 322, as indicated by the arrow 342 This draws the distal end of the inner cylindrical shell 322 into the outer shell 324, while the remainder of the inner shell remains stationary, relative to the shaft 305. As the outer shell 324 continues to slide proximally, the shaft 305 becomes progressively more exposed at its distal end, as shown in FIG. 3d. This process continues until the shaft 305 has been completely exposed and the outer cover 310 has been removed from the body. If after removal of the outer cover 310, a new detachable outer cover (not shown) becomes exposed on the shaft, the newly exposed detachable layer may later on be removed from the device.

Fourth Embodiment

Figure 4A:
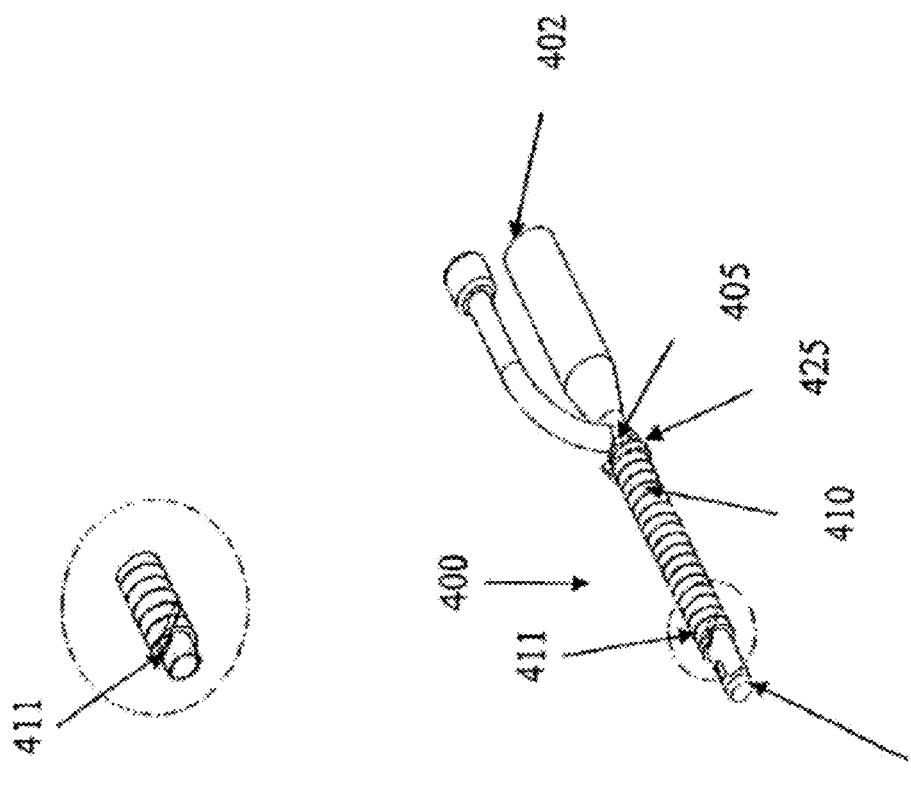
FIGS. 4a-4c show an indwelling device having a helical cover in accordance with another embodiment of the invention.
Figure 4:
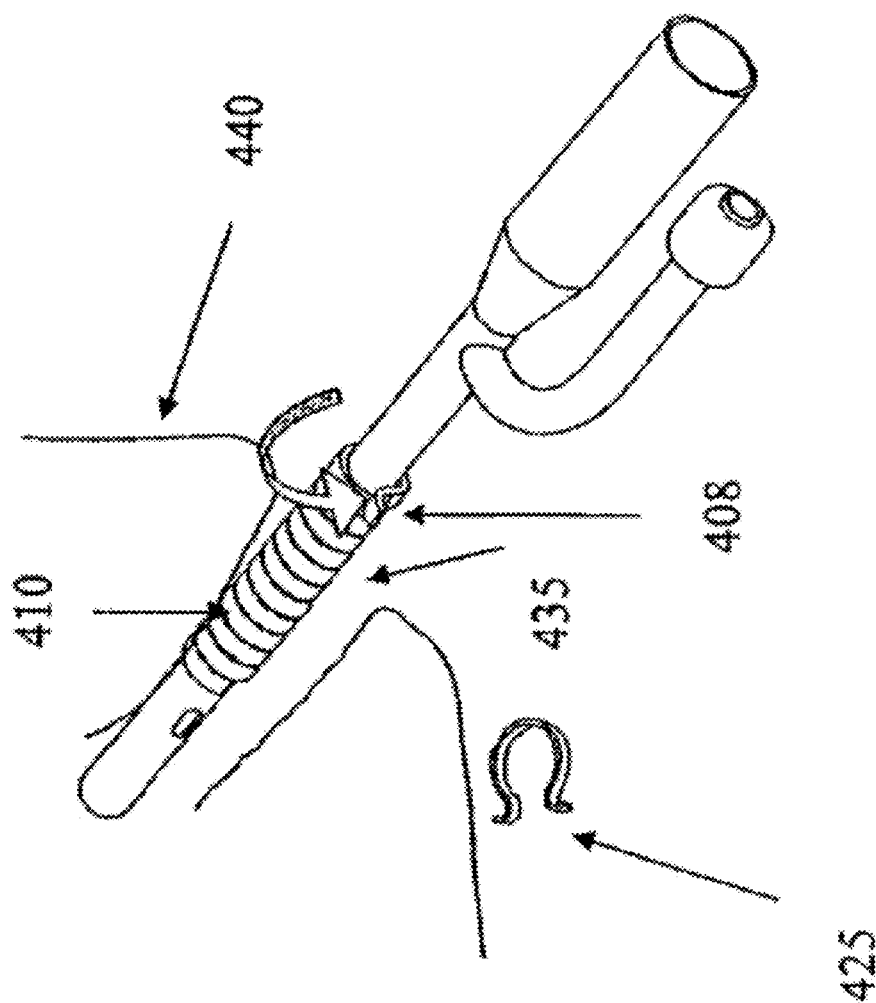

FIG. 4a shows an indwelling device 400 in accordance with another embodiment of the invention. The device 400 has a proximal end 402, a distal end 404, and a cylindrical shaft 405 that may be solid or hollow. The shaft 405 is contained in an outer cover 410 having the general shape of a thin cylindrical shell. The outer cover 410 is formed from a strip of biocompatible material, such as latex or silicone rubber. The outer cover 410 is formed by winding the strip of biocompatible material in a helical pattern around the length of the shaft 405. Consecutive turns of the helix overlap so as to completely cover the shaft 405. The distal end 411 of the strip is tucked under the first few turns of the helix, so as to immobilize the distal end of the strip as shown in the insert to FIG. 4a. The proximal end of the strip is held in place by a ring 425. The ring 425 has a lumen dimensioned to fit snugly on the shaft 405 and the proximal end of the outer cover 410. This prevents slipping of the outer cover 410 over the shaft 405 during insertion of the device 400 into the body, and maintains the outer cover 410 on the shaft 405 after insertion.

FIG. 4b shows the device of FIG. 4a after insertion into the body. The device 400 was inserted into the body through a hole 435 on the body surface 440. The hole 435 may be a natural hole on the body surface (e.g. mouth, meatus, nostrils, etc.) or an artificial hole (e.g. a hole formed in the skin by a surgical incision). After insertion, the proximal end of the device 400, including the ring 425, extends through the hole 435 and is exposed on the body surface. This is by way of example only, and the device may in use be completely enclosed within the body. In this case, a surgical cut is made in order to access the proximal end of the device 400 and the ring 425. Relative movement of the shaft 405 and the outer cover 410 is prevented during insertion due to the radial force of the ring 425 on the proximal end of the outer cover 410, and the radial force of the last few turns of the helix on the distal end of the outer cover 410.

At any time after insertion, the outer cover 410 may be detached from the device 400. Referring to FIG. 4c, the ring 425 is removed from the shaft 405 and the outer cover 410 is unwound from its proximal end 408. (FIG. 4c). The outer cover 410 continues to be unwound, until the distal end of the outer cover 410 is freed. The proximal end of the outer cover 410 may now be grasped and manually removed from the body leaving the device 400 in place. If after removal of the outer cover 410, a new detachable outer cover (not shown) becomes exposed on the shaft, the newly exposed detachable layer may later on be removed from the device.

Fifth Embodiment

Figure 5B:
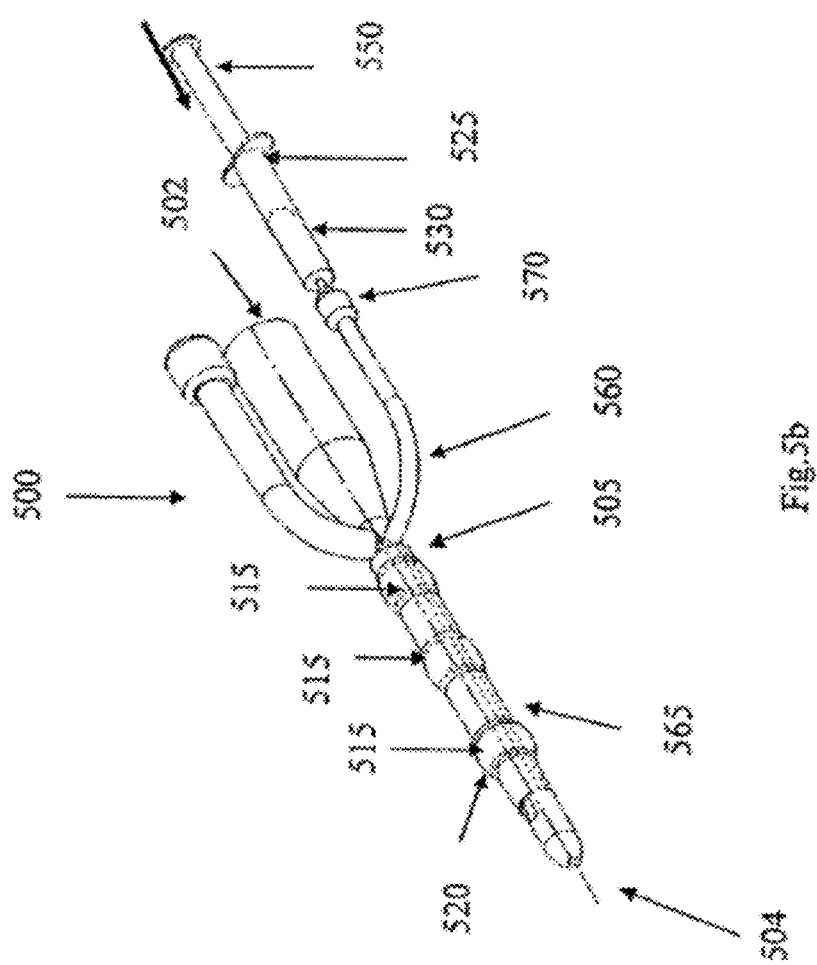

FIG. 5a shows an indwelling device 500 in accordance with another embodiment of the invention. The device 500 has a proximal end 502, a distal end 504, and a cylindrical shaft 505 that may be solid or hollow. The shaft 505 is contained in an outer cover 510 having the general shape of a thin cylindrical shell. The outer cover 510 is formed from a biocompatible, rigid material, such as plastic or metal. One or more balloons 515 are located in a space 520 formed between the outer cover 510 and the shaft 505. In FIG. 5a, the balloons are shown in their deflated state. As shown in FIG. 5b, before inserting the device 500 into the body, the balloons 515 are inflated with a fluid such as air or water. A syringe 525 containing the fluid 530 is inserted into a valve 570.

The balloons are inflated by opening the valve 570 and depressing the plunger 550 of the syringe. The fluid 530 is conducted from the syringe 525 through a first tube 560 and then through a second tube 565 running along the shaft 505 and then into each of the balloons 515. When inflated, the balloons apply a pressure to both the shaft 515 and the outer cover 510. The valve 540 is then closed to prevent fluid from leaving the balloons. The outer cover 510 thus becomes reversibly attached to the shaft 505 by the balloons 515 that are lodged between the outer cover 510 and the shaft 505.

Figure 5D:
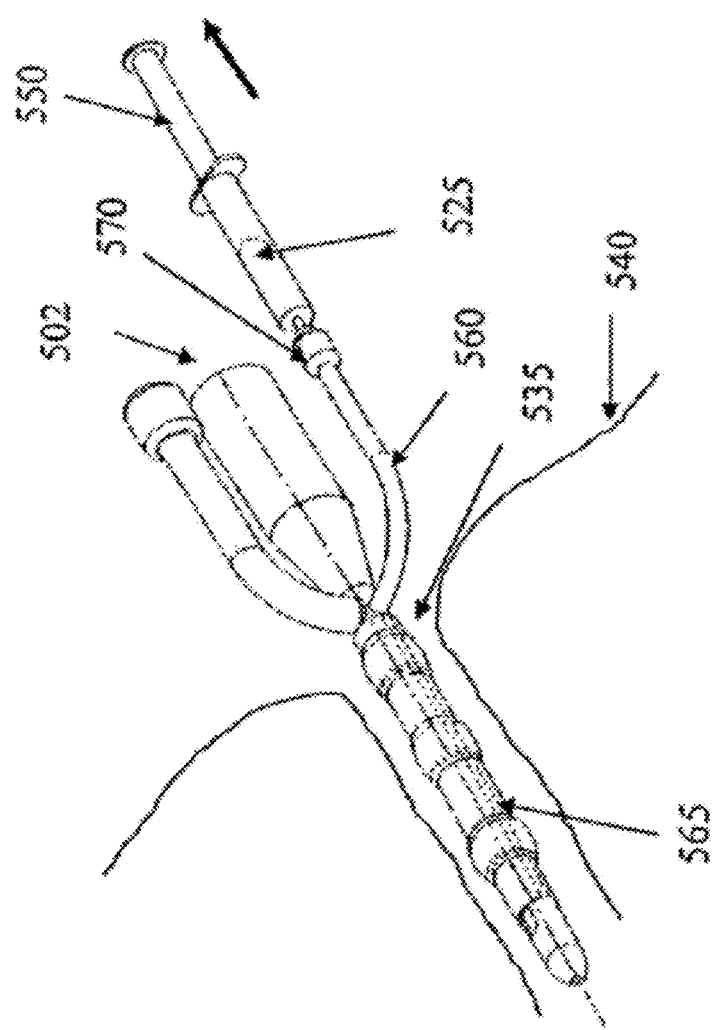
Figure 5E:
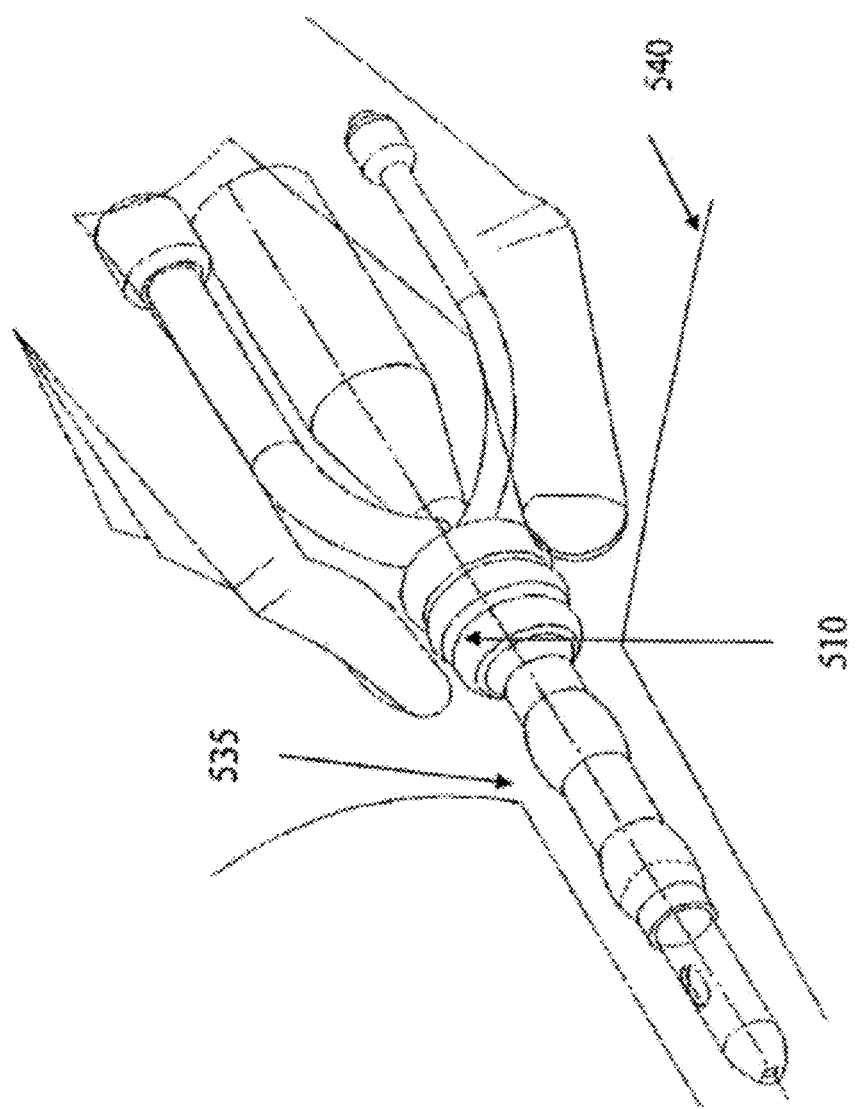

FIG. 5c shows the device of FIGS. 5 and b after insertion into the body. The device 500 was inserted into the body through a hole 535 on the body surface 540. The hole 535 may be a natural hole on the body surface (e.g. mouth, meatus, nostrils, etc.) or an artificial hole (e.g. a hole formed in the skin by a surgical incision). After insertion, the proximal end of the device extends through the hole 535 and is exposed on the body surface. This is by way of example only, and the device may in use be completely enclosed within the body. In this case, a surgical cut is made in order to access the proximal end of the cover 510.

At any time after insertion, the outer cover 510 may be detached from the device 100 by deflating the balloons 515. This may be done, for example, by inserting the syringe 530 into the valve 570 and drawing the fluid from the balloons so as to puncture the balloon by pulling on the plunger 550. Once the balloons have been deflated, the proximal end of the device 500 may be grasped and manually removed from the body leaving the device 500 in place. If after removal of the outer cover 510, a new detachable outer cover (not shown) becomes exposed on the shaft, the newly exposed detachable layer may later on be removed from the device.

Sixth Embodiment

FIG. 7 shows an indwelling device 700 in accordance with another embodiment of the invention. The device 700 has a proximal end 702, a distal end 704, and a hollow cylindrical shaft 705. The shaft 705 has a lumen 708. In this embodiment, the cover 710 lines the inner surface of the hollow shaft 705. The lumen 708 contains a cover 710 having the general shape of a thin cylindrical shell covering the wall of the lumen 708. The cover 710 is formed from a biocompatible, rigid material, such as plastic. The proximal end of the cover 710 is glued to the lumen of a restraining ring 711. A circumferential clamp 750 around the ring 711 secures the ring 711 to the proximal end 702 of the device 700.

Figure 7A:
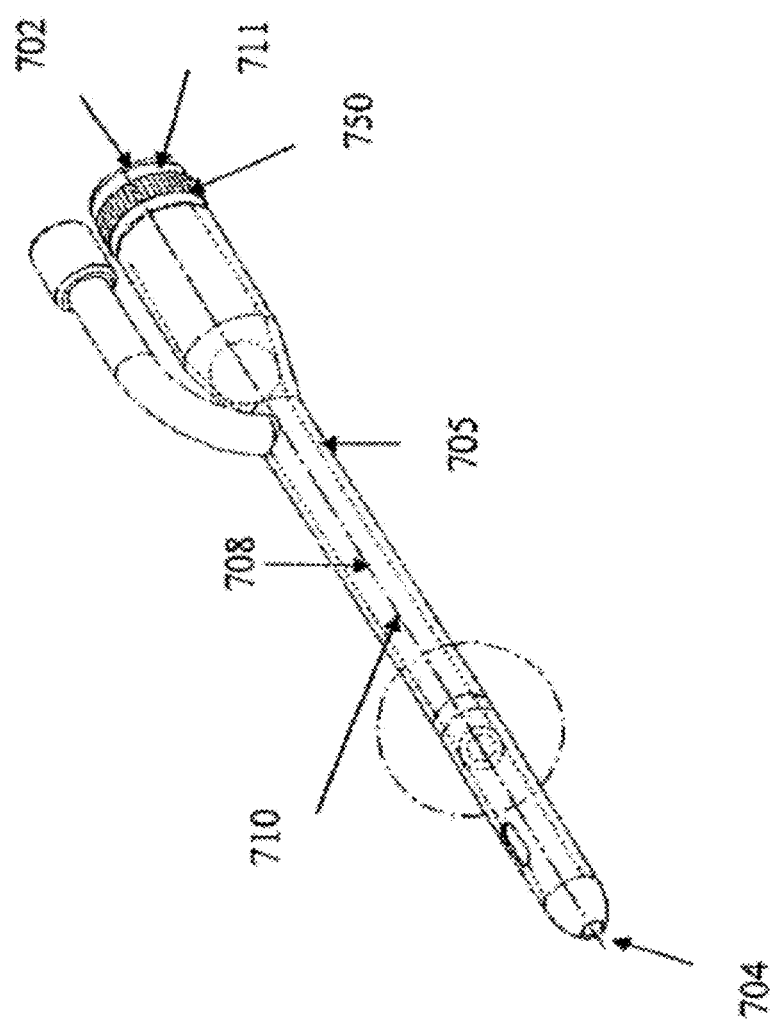

FIG. 7b shows the catheter of FIG. 7a after insertion into the body. The catheter 700 was inserted into the body through a hole 735 on the body surface 740. The hole 735 may be a natural hole on the body surface (e.g. mouth, meatus, nostrils, etc.) or an artificial hole (e.g. a hole formed in the skin by a surgical incision). After insertion, the proximal end of the device extends through the hole 735 and is exposed on the body surface. This is by way of example only, and the device may in use be completely enclosed within the body. In this case, a surgical cut is made in order to access the proximal end of the device 700.

FIG. 7b further shows removal of the outer cover. The ring 711 is detached from the proximal end 702 of the device 700, and the ring 711 is removed from the device 700 together with the cover 710 attached to it. As the ring 711 continues to be pulled away from the proximal end 702 of the device 700, the cover 710 becomes attenuated and detaches from the inner surface of the shaft lumen 708. If after removal of the outer cover 710, a new detachable outer cover (not shown) becomes exposed on the shaft, the newly exposed detachable layer may later on be removed from the device.

Seventh Embodiment

FIG. 8a shows an indwelling device 800 in accordance with a further embodiment of the invention. The device 800 has a proximal end 802, a distal end 804, and a cylindrical shaft 805 that may be solid or hollow. The shaft 805 is contained in an outer cover 810 having the general shape of a thin cylindrical shell. The outer cover 810 is formed from a biocompatible, elastic material, such as latex, that was stretched over the shaft 805, and allowed to contract on the shaft 805. The outer cover 810 is reversibly attached to the shaft 805 by circumferential elastic forces in the outer cover 810 that are exerted on the shaft 805. This prevents slipping of the outer cover 810 over the shaft 805 during insertion of the device 800 into the body, and maintains the outer cover 810 on the shaft 805 after insertion.

The outer cover 810 has a line of perforations 820 extending along the length of the outer cover 810. A ring 811 located on the shaft 805 contains a cord 830 that fixes the proximal end of the cover 810 onto the shaft 805. As shown in FIG. 6, the device 800 may optionally comprise a distally located annular clamp 615 that secures the distal end of the outer cover 810 to the shaft 805 and prevents debris from accumulating under the distal end of the outer cover 810 during insertion.

FIG. 8b shows the device 800 after insertion into the body. The device 800 was inserted into the body through a hole 835 on the body surface 840. The hole 835 may be a natural hole on the body surface (e.g. mouth, meatus, nostrils, etc.) or an artificial hole (e.g. a hole formed in the skin by a surgical incision). After insertion, the proximal end of the device 800 extends through the hole 835 and is exposed on the body surface. This is by way of example only, and the device may in use be completely enclosed within the body. In this case, a surgical cut is made in order to access the proximal end of the cord 830. Relative movement of the shaft 805 and the outer cover 810 is prevented during insertion due to the circumferential elastic forces of the outer cover 810 on the shaft 805.

Figure 8C:
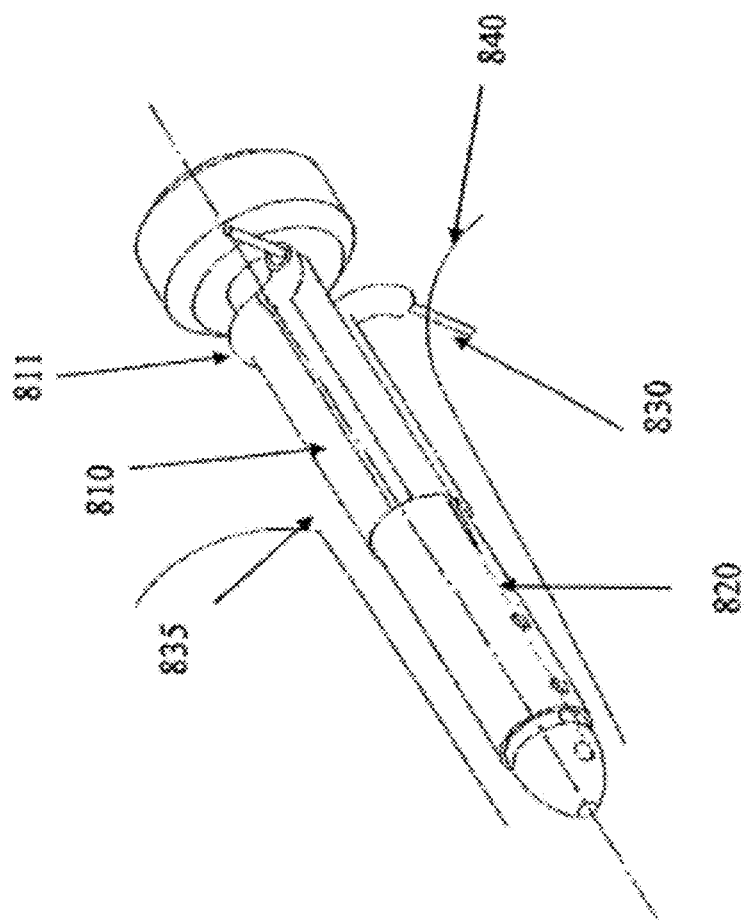
Figure 8D:
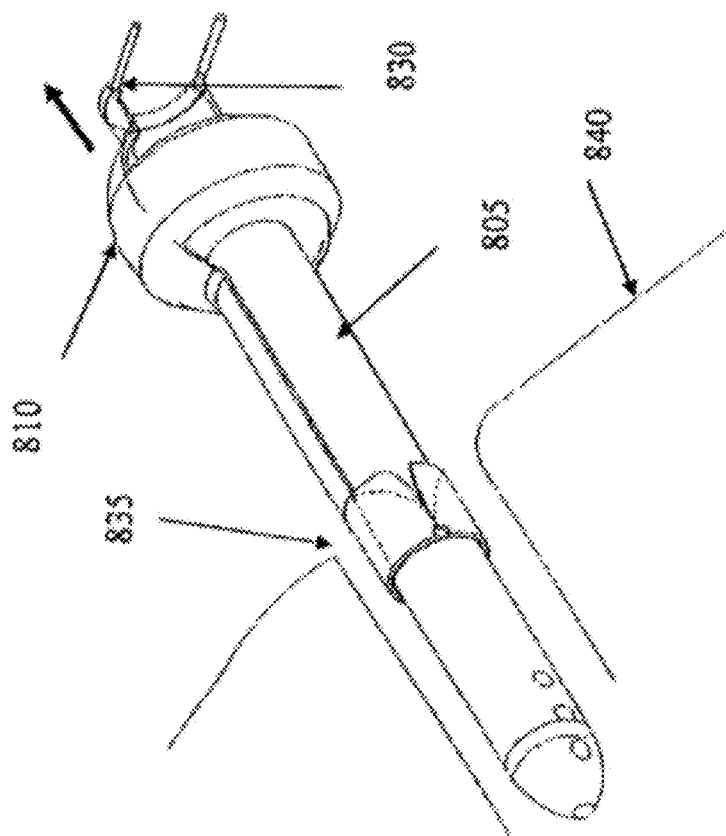

At any time after insertion, the outer cover 810 may be detached from the device 800. The cord 830 is released as shown in FIG. 8c. The proximal end of the perforation 820 is then torn. The cover 810 is then made to slide proximally over the shaft 805 as shown in FIG. 8d. This causes a new region of the perforation 820 to be exposed outside the body. This section of the perforation is then torn, and the cover 810 is then made to slide proximally over the shaft 805 (FIG. 8d). This process continues until all of the perforation 820 is completely torn and the cover is removed from the body. If after the removal of the outer cover 810, a new detachable outer cover (not shown) becomes exposed on the shaft, the newly exposed detachable layer may later on be removed from the device.

Eighth Embodiment

Figure 11A:
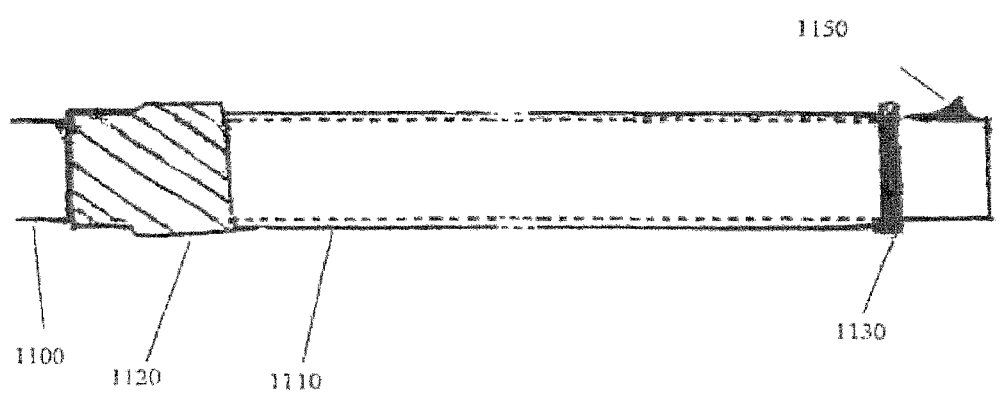
FIGS. 11a-11d show an indwelling device having a cover attached to its outer surface, said cover being fitted with proximal and distal sealing elements and a fixed cutting blade.
Figure 11B:
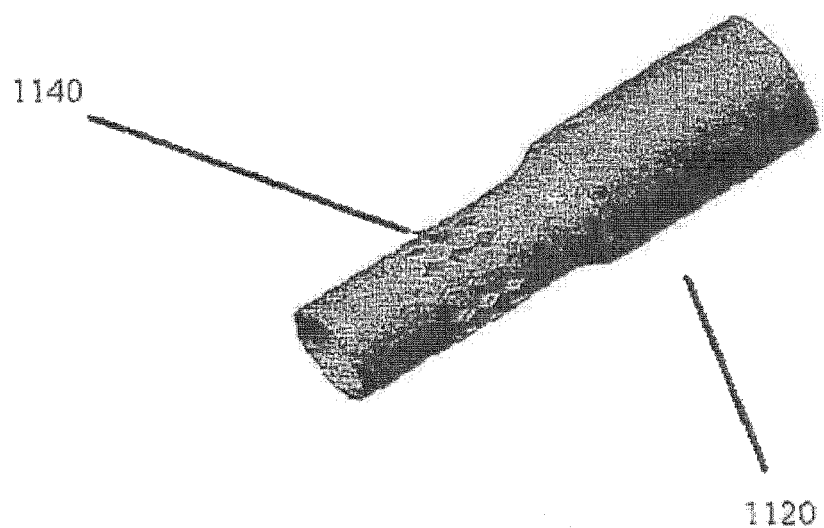

FIG. 11a depicts a further embodiment of the device of the present invention, comprising an elongate catheter 1100 bearing an outer cover 1110 on its external surface. The cover 1110 is situated in close apposition to the outer surface of catheter 1100 along almost the entire length thereof. In some versions of this embodiment, the cover may extend over the entire length of the device. In addition, two sealing elements—a distal sealing tip 1120 and a proximal sealing element 1130—ensure that cover 1110 and the outer surface of catheter 1100 are in very close contact at their distal and proximal ends respectively, thus preventing the passage of possibly contaminating fluids (e.g. blood, urine, tissue fluid) between said catheter and said outer cover. In the typical device according to this embodiment shown in FIG. 11a, the distal sealing tip 1120 is elongate in shape, while the proximal sealing element 1130 is depicted as an annular ring. FIG. 11b depicts an alternative version of elongated distal sealing tip 1120. The function of the perforations 1140 present in the distal half of this version of the sealing element is to provide a fluid pathway for use in cases in which it is desired that substances such as pharmaceutical agents and the like will be released from the indwelling device into the blood stream, duct or tissues. In yet other alternative forms of the distal sealing tip 1120, the internal side of the distal half of the sealing tip, in which are present one or more apertures or perforations, may be covered with a mesh, thereby providing mechanical support and strength without interfering with the desired fluid flow channel provided by said apertures. It is to be further noted that it is possible to use many other shapes and forms of sealing elements, all of which are included in the scope of the present invention.

According to one embodiment of the invention, a thin layer of mineral oil or similar biocompatible fluid is present between each adjacent pair of covers (in the case that the device is fitted with a sequential stack of covers, as described hereinabove) and/or between the innermost cover and the indwelling medical device itself. The presence of the interlayer oil is advantageous both in providing an extra mechanism for preventing the ingress of contaminating fluids, as well as acting as a lubricant in order to facilitate the removal of the layer(s) from each other and/or from the surface of the medical device. In the case that mineral oil is incorporated into the device as described herein, the sealing elements may usefully be constructed of an oil-absorbing material.

In one particularly embodiment of this type of device, both the outer cover 1110 and the distal sealing tip 1120 are made of medical grade polyurethane. In such a case, however, the polyurethane used to construct the cover 1110 will usually be of a harder grade (i.e. have a higher Shore rating) than that used to manufacture the sealing tip 1120. However, other biocompatible materials such as silicones, PVC, mylar and nylon may also be used to manufacture the outer cover 1110 and distal sealing tip 1120.

The proximal sealing element 1130 is most conveniently manufactured from polyurethane, but any other suitable material such as silicones, PVC, mylar and nylon may also be employed, and as such fall within the scope of the present invention as claimed.

The abovementioned materials that may be used to construct the medical device (e.g. catheter), outer cover and proximal and distal sealing elements may be used in any of the available degrees of hardness and color (including colorless transparent). In addition, any of these materials may be prepared such that they incorporate radio-opaque substances, for use as markers, as is known in the art. The embodiment of the device shown in FIG. 11*a* also incorporates a stationary cutting blade 1150 in its proximal, preferably extra-corporeal, portion. As shown in FIG. 11*a*, the proximal sealing element 1130 may be situated external to (and separate from) the blade. Alternatively, said element may be mounted close to the blade, within the blade housing itself (not shown).

Blade 1150 is used to assist in the removal of the outer cover 1110 (together with its attached biofilm deposits) in the following manner. Firstly, in the event that proximal sealing element 1130 is situated external to blade 1150 (as indicated in FIG. 11*a*), said element is opened and removed from the device and (if necessary) from the body. In the event that the proximal sealing element exists as an integral part of the blade housing, this stage is not required. In a further version of this embodiment of the invention, the proximal sealing element is constructed such that it may adopt two different conformations. In the first of these conformations, the sealing element is capable of preventing ingress of fluids into the space between the proximal end of the covers(s) and the medical device. In the second of these conformations, the proximal sealing element adopts a position such that the tight seal between the cover and underlying medical device is lost in the region of said element, thereby facilitating the removal of the cover layer and any biofilm attached thereto. Consequently, when the device is constructed in this manner, the first stage of the cover removal process consists of changing the conformation of the proximal sealing element from the first conformation to the second conformation.

The proximal margins of the outer cover 1110 are then grasped between the operator's fingers and drawn in a proximal direction toward the blade 1150. Upon making contact with the blade, outer cover 1110 is incised at its free edge. This initial incision becomes elongated as the proximal margins of cover 1110 are drawn still further in a proximal direction, until the entire length of said cover has been cut longitudinally, and removed from contact with the catheter 1100 and finally entirely withdrawn from the body.

Figure 11C:
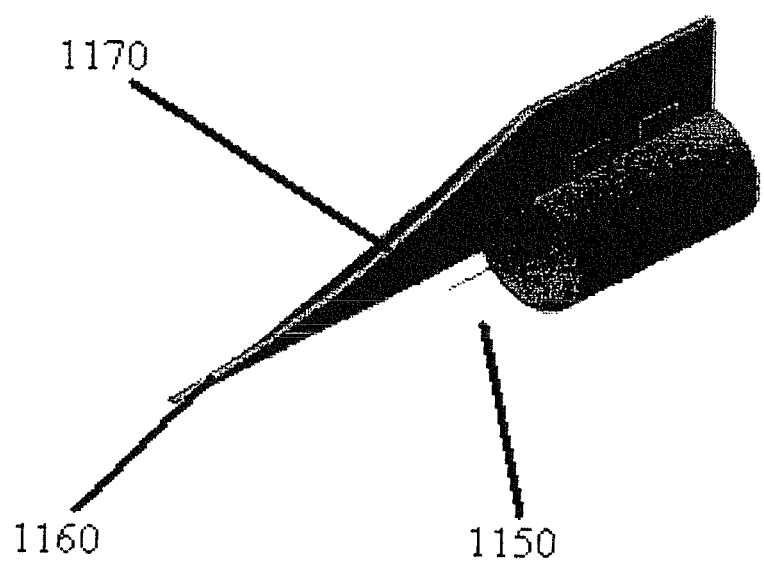

FIG. 11*c* illustrates the shape and form of cutting blade assembly 1150 in greater detail. The distal, ramp-like portion 1160 of the blade possesses a rounded, non-sharp profile which leads into the cutting edge 1170 of the blade assembly. It will thus be appreciated that when, as described hereinabove, the outer cover 1110 is drawn in a proximal direction towards cutting blade assembly 1150, the distal, ramp-like portion 1160 will serve to guide the free proximal margin of said cover towards cutting edge 1170. This guiding mechanism serves to prevent the kinking or buckling of cover 1110 that might otherwise occur if the proximal margin of said cover were to encounter a sharp, angled blade.

The cutting blade 1150 may be constructed from any suitable material that will permit said assembly to function as described hereinabove. In one embodiment, however, the material used to construct the cutting blade 1150 is constructed from a sharpened metal such as medical grade stainless steel. In other embodiments, the blade may be constructed from other suitable biocompatible metals, as well as from rigid plastic materials.

Figure 11D:
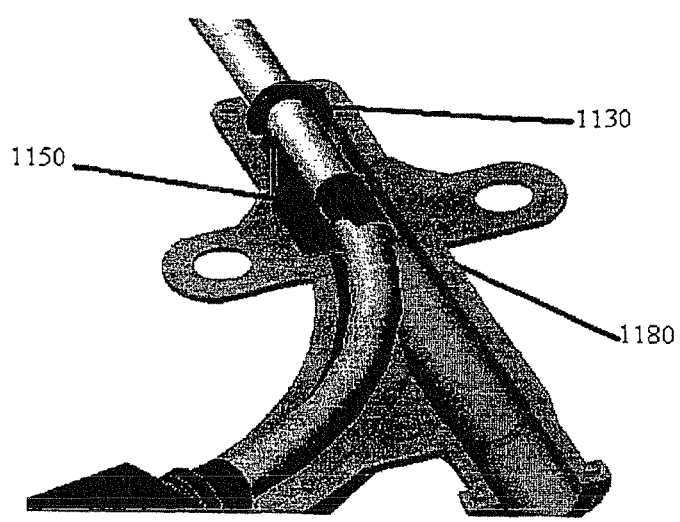

The cutting blade assembly 1150 may be mounted in a stationary position at any convenient point at the proximal end of the device. In a particularly one embodiment, as shown in the exploded view given in FIG. 11*d*, cutting blade assembly 1150 is located within a multiple luer lock fitting 1180, of any of the types that are well known in the art.

It is to be emphasized that the various components described in this embodiment of the device of the invention (i.e. the distal and proximal sealing elements and the stationary cutting blade) may all be incorporated into a single device, as illustrated in FIG. 11*a*. Alternatively, a single device may incorporate only one or two of the three elements disclosed hereinabove. It should further be noted that the presently-described embodiment is suitable for use both in conjunction with a single cover and with a stack of covers, as is the case with the other embodiments disclosed and described hereinabove.

FIG. 12*a* illustrates a medical device with one hole at the distal end of the device, having a cover attached to its outer surface with a sealing element according to some embodiments of the present invention. This embodiment provide the basic cover 1230 with a single sealing element 1220 adapted for medical device having one hole 140 at the distal end of the medical device. According to this embodiment the cover is integrated with the seal element, encapsulating the medical device by covering the medical device surface, while maintaining free passage from the hole at the distal end of the device to the body in which the medical device is inserted. The seal element 1220 prevents the ingress of fluids between the cover and at least part of the medical device such as part of the remaining part of the medical device is fully covered and sealed.

FIG. 12*b* illustrates a medical device with more than one hole having a cover attached to its outer surface with a sealing element according to some embodiments of the present invention. This embodiment demonstrates the basic cover with a single seal element as applied with medical device having at least one surface hole such as holes: 1250 and 1260. As can be seen in this figure, the distal area part of medical device surface remains uncovered to allow free passage from all surface holes to the body. Accordingly such solution provides partial coverage of the surface.

Figure 13:
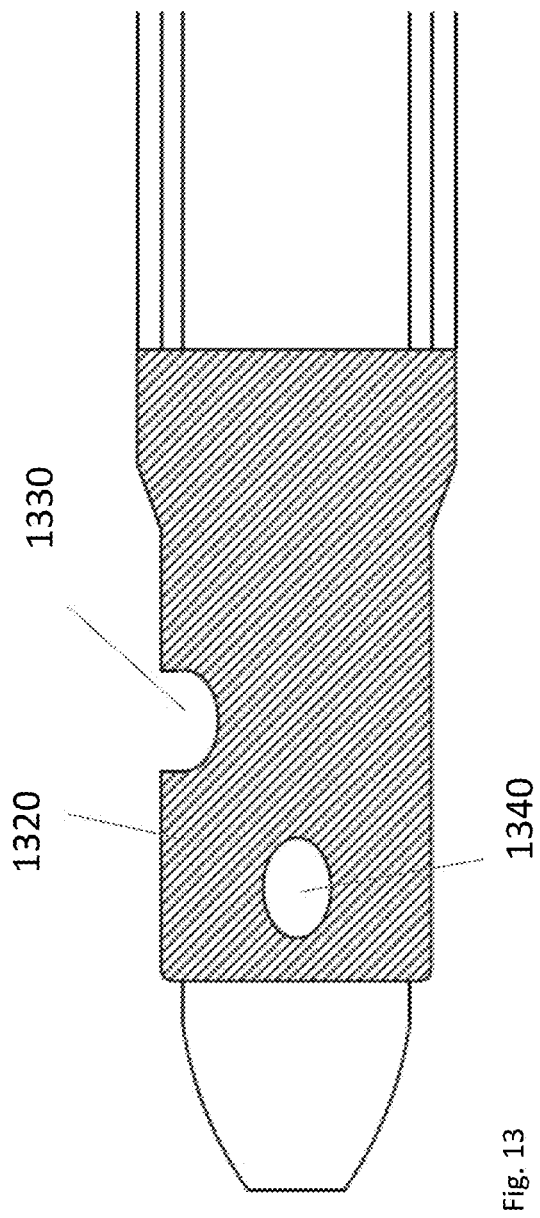
FIG. 13 illustrates a medical device with more than one hole having a cover attached to its outer surface with a single sealing element having at least one hole according to some embodiments of the present invention.

The following embodiments provide different covering and sealing solutions for medical devices having multiple holes, for encapsulating the medical device though it's length, covering the at least one surface hole, while maintaining full free passage, from the holes FIG. 13 illustrates a medical device with more than one hole having a cover attached to its outer surface with a single sealing element having at least one seal hole according to some embodiments of the present invention. This embodiment provides a cover integrated with a single sealing element, where the sealing element includes at least one seal hole. In this example two seal holes 1340 and 1330 are used, each hole corresponding to different surface holes (1250 and 1260 as seen in FIG. 12). Such structure of the sealing element encapsulating the medical device though it's length, while maintaining free passage from each surface hole to the body of the subject.

Figure 14:
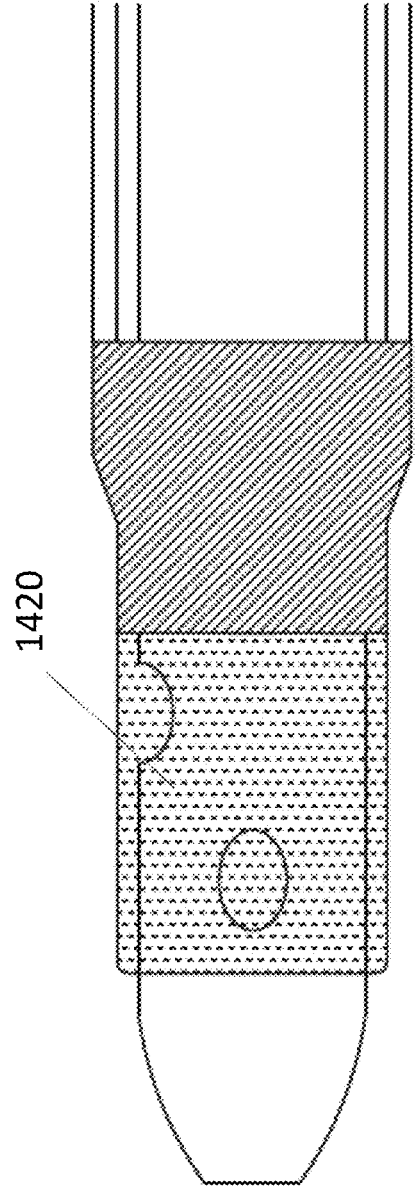
FIG. 14 illustrates a medical device with more than one hole having a cover attached to its outer surface with a single sealing element having plurality of holes according to some embodiments of the present invention.

FIG. 14 illustrates a medical device with more than one hole having a cover attached to its outer surface with a single sealing element having plurality of holes according to some embodiments of the present invention. This embodiment provides a cover integrated with a single sealing element, where the sealing element is partly sealed and partly having perforation structure, net structure, or plurality of holes. Such structure of the sealing element encapsulates the medical device though it's length while maintaining free passage from each surface hole to the body. The design of the sealing element is adapted to different designs of surface holes disregard of their exact location along the surface.

FIG. 15 illustrates a medical device with more than one hole having a cover attached to its outer surface with more than one sealing element having holes according to some embodiments of the present invention. The cover structure according to this embodiment is integration of cover elements interlaced? with seal elements. The integration is designed to be adapted to the surface hole distribution along the medical device: a sealing elements (1420, 1440, 1560) is positioned in-between two successive surface holes (1470, 1480) and a cover elements 1430. 1450 overlaps the surface holes in-between the sealing elements. Each cover element has a cover hole corresponding to a surface hole. At least one hole is isolated from other holes by at least one sealing element.

Figure 16A:
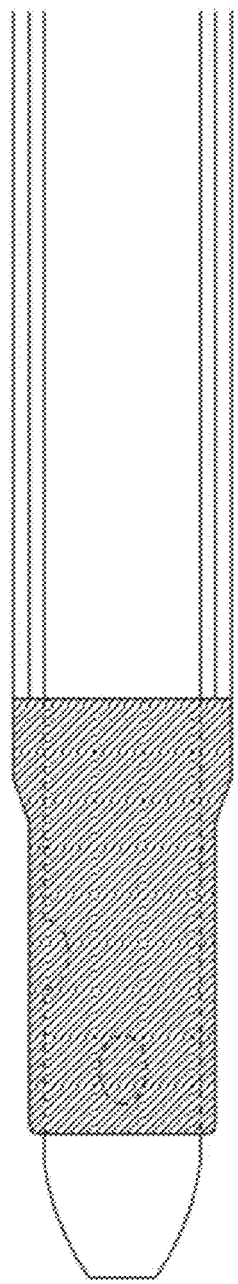
FIGS. 16A B illustrates a medical device with more than one hole having a cover attached to its outer surface with a single sealing element enabling delayed exposure of at least one hole according to some embodiments of the present invention.
Figure 16B:
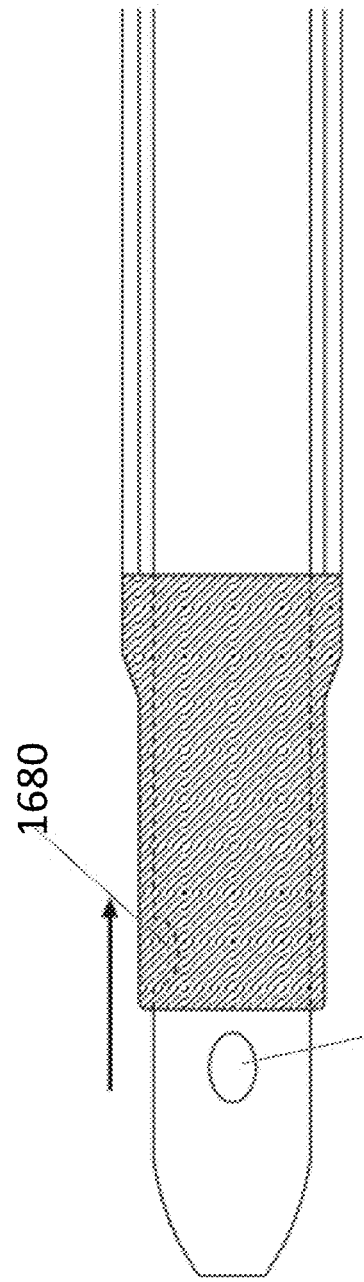

FIGS. 16A and B illustrate a medical device with more than one hole having a cover attached to its outer surface with a single sealing element according to some embodiments of the present invention. This embodiment refers to usage scenario where some of the surface holes are to be exposed in delayed time periods, hence in the first stage (FIG. 16*a*) the seal element covers the surface holes preventing free passage from at least one surface hole to the body. According to medical procedures, the cover is pulled out at least partly and the sealing element moves proximally (FIG. 16B), exposing at least one surface hole (1670) to the body at the distal part of the medical device.

While specific embodiments of the invention have been described for the purpose of illustration, it will be understood that the invention may be carried out in practice by skilled persons with many modifications, variations and adaptations, without departing from its spirit or exceeding the scope of the claims.

What is claimed is:

1. A medical device for insertion into a body, the device having at least one surface covered by and attached to at least one detachable cover and at least one surface hole, the cover being detachable from the surface and removed from the body any time after the device has been inserted in the body,
wherein the cover and the device are inserted in the body as a united device, such that the cover encapsulates and seals the medical device,
wherein the cover can be detached and pulled off the device which remains in the body,
wherein the device cannot be pulled out from the cover while the cover remains within the body,
wherein the cover includes at least one sealing element for preventing ingress of fluids between the cover and at least part of the medical device;
wherein the cover and the at least one sealing element, encapsulates the medical device through its length, overlapping at least one surface hole;
wherein the cover and the at least one sealing element are designed to isolate at least one hole, while enabling free passage through said hole, in at least partial time period through which the medical device is within the body;
wherein said medical device is selected from the group consisting of: (a) a catheter; (b) a cannula; (c) a drain; (d) a stent; (e) a pacemaker; and (f) an electrode.

2. The medical device of claim 1, wherein the seal element covers partial surface of the device in which the at least one surface hole is located and includes at least one seal hole, wherein each seal hole overlaps at least one surface hole and is located over at least one surface hole of the medical device.

3. The medical device of claim 1, wherein the seal element covers partial surface of the device in which the at least one surface hole is located and parts of the seal element has a perforation structure or a net structure.

4. The medical device of claim 1, wherein the cover integrates more than one seal element, where each seal element is located between two cover parts and isolates the at least one surface hole, where each cover part corresponds to different surface hole.

5. The medical device of claim 4, wherein at least one cover element has at least one cover hole corresponding to at least one surface hole.

6. The medical device of claim 4, wherein at least each cover has a perforation structure or a net structure.

7. The medical device of claim 1, wherein the seal element covers a partial surface of the device where the at least one hole is located, wherein the cover can be pulled out at least partially, such as, at least part of the surface in which one hole is located is exposed.

8. The medical device of claim 7 wherein the other parts of medical device surface are remained covered.

9. The device according to claim 1, wherein the sealing element is formed from a material selected from the group consisting of: (a) rubber; (b) silicone rubber; (c) polyvinylchloride; (d) latex; (e) woven metal mesh; parylene; (g) polyurethane; (h) mylar; and (i) nylon.

10. The device according to claim 1, wherein said device is a urinary catheter.

11. The device according to claim 1, wherein said device is a venous catheter.

12. The device according to claim 1, wherein said device is a dialysis catheter.

13. The device according to claim 1, having a stack of at least two sequentially detachable covers, each cover being detachable either from the surface of the device or from the adjacent cover, and removed from the body while the device is within the body.

14. The device according to claim 1, wherein the cover is formed from a material selected from the group consisting of: (a) rubber; (b) silicone rubber; (c) polyvinylchloride; (d) latex; (e) woven metal mesh; parylene; (g) polyurethane; (h) mylar; and (i) nylon.

15. The device according to claim 1, wherein the cover or sealing element are formed from a biocompatible material.

16. The device according to claim 1, wherein the cover or the sealing element is formed from a non-allergenic material.

17. The device according to claim 1, wherein the cover is impenetrable to microorganisms.

18. The device according to claim 1, wherein the cover is impenetrable to water.

19. The device according to claim 1 wherein the cover stores and releases a substance.

20. The device according to claim 1, wherein the substance is an anti-microbial or anti-fungal compound.

21. The device according to claim 1, wherein the sealing element is made of polyurethane.

* * * * *